(12) United States Patent
Buiser et al.

(10) Patent No.: US 7,588,780 B2
(45) Date of Patent: *Sep. 15, 2009

(54) EMBOLIZATION

(75) Inventors: Marcia Buiser, Watertown, MA (US);
Marc Bellisario, Stoneham, MA (US);
David Knapp, Shoreview, MN (US);
Stephan Mangin, Ashland, MA (US);
Janel Lanphere, Newton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 530 days.

This patent is subject to a terminal disclaimer.

(21) Appl. No.: 10/215,594

(22) Filed: Aug. 9, 2002

(65) Prior Publication Data

US 2003/0185896 A1    Oct. 2, 2003

Related U.S. Application Data

(63) Continuation-in-part of application No. 10/109,966, filed on Mar. 29, 2002.

(51) Int. Cl.
*A61K 9/14* (2006.01)
*A61K 9/50* (2006.01)
*B01J 13/02* (2006.01)
*B32B 15/02* (2006.01)

(52) U.S. Cl. .................. 424/501; 424/489; 264/4.1; 264/4.33; 264/4.7; 427/213.34; 428/402.21

(58) Field of Classification Search .............. 424/489, 424/501; 264/4.1, 4.33, 4.7; 427/213.34; 428/402.21

See application file for complete search history.

(56) References Cited

U.S. PATENT DOCUMENTS

| 2,275,154 A | 3/1942 | Merrill et al. |
| 2,609,347 A | 9/1952 | Wilson |
| 3,663,470 A | 5/1972 | Nishimura et al. |
| 3,737,398 A | 6/1973 | Yamaguchi |
| 3,957,933 A | 5/1976 | Egli et al. |
| 4,025,686 A | 5/1977 | Zion |
| 4,034,759 A | 7/1977 | Haerr |
| 4,055,377 A | 10/1977 | Erickson et al. |
| 4,076,640 A | 2/1978 | Forgensi et al. |
| 4,094,848 A | 6/1978 | Naito |
| 4,096,230 A | 6/1978 | Haerr |
| 4,098,728 A | 7/1978 | Rosenblatt |
| 4,110,529 A | 8/1978 | Stoy |

(Continued)

FOREIGN PATENT DOCUMENTS

AU    A-76186/98    10/1998

(Continued)

OTHER PUBLICATIONS

Kanebo Ltd, "Porous Spherical Particles and the Preparation Processfor Preparing thereof", Feb. 11, 2001.*

(Continued)

*Primary Examiner*—Carlos A. Azpuru
(74) *Attorney, Agent, or Firm*—Fish & Richardson P.C.

(57) ABSTRACT

Embolic polymer particles are described. For example, the particles include pores such that the predominant size of pores near the center of the particles is greater than the predominant size of pores adjacent to periphery of the particle

48 Claims, 13 Drawing Sheets

U.S. PATENT DOCUMENTS

| | | | |
|---|---|---|---|
| 4,159,719 A | 7/1979 | Haerr | |
| 4,191,672 A | 3/1980 | Salome et al. | |
| 4,198,318 A | 4/1980 | Stowell et al. | |
| 4,243,794 A | 1/1981 | White et al. | |
| 4,246,208 A | 1/1981 | Dundas | |
| 4,266,030 A | 5/1981 | Tschang et al. | |
| 4,268,495 A | 5/1981 | Muxfeldt et al. | |
| 4,271,281 A | 6/1981 | Kelley et al. | |
| 4,402,319 A | 9/1983 | Handa et al. | |
| 4,413,070 A | 11/1983 | Rembaum | |
| 4,427,794 A | 1/1984 | Lange et al. | |
| 4,428,869 A | 1/1984 | Munteanu et al. | |
| 4,429,062 A | 1/1984 | Pasztor et al. | |
| 4,442,843 A | 4/1984 | Rasor et al. | |
| 4,444,961 A | 4/1984 | Timm | |
| 4,452,773 A | 6/1984 | Molday | |
| 4,456,693 A | 6/1984 | Welsh | |
| 4,459,145 A | 7/1984 | Elsholz | |
| 4,472,552 A | 9/1984 | Blouin | |
| 4,477,255 A | 10/1984 | Pasztor et al. | |
| 4,492,720 A | 1/1985 | Mosier | |
| 4,522,953 A | 6/1985 | Barby et al. | |
| 4,542,178 A | 9/1985 | Zimmermann et al. | |
| 4,551,132 A | 11/1985 | Pasztor et al. | |
| 4,551,436 A | 11/1985 | Johnson et al. | |
| 4,573,967 A | 3/1986 | Hargrove et al. | |
| 4,622,362 A | 11/1986 | Rembaum | |
| 4,623,706 A | 11/1986 | Timm et al. | |
| 4,640,807 A | 2/1987 | Afghan et al. | |
| 4,657,756 A | 4/1987 | Rasor et al. | |
| 4,661,137 A | 4/1987 | Garnier et al. | |
| 4,663,358 A | 5/1987 | Hyon et al. | |
| 4,671,954 A | 6/1987 | Goldberg et al. | |
| 4,674,480 A | 6/1987 | Lemelson | |
| 4,675,113 A | 6/1987 | Graves et al. | |
| 4,678,710 A | 7/1987 | Sakimoto et al. | |
| 4,678,814 A | 7/1987 | Rembaum | |
| 4,680,320 A | 7/1987 | Uku et al. | |
| 4,681,119 A | 7/1987 | Rasor et al. | |
| 4,695,466 A | 9/1987 | Morishita et al. | |
| 4,713,076 A | 12/1987 | Draenert | |
| 4,742,086 A | 5/1988 | Masamizu et al. | |
| 4,743,507 A | 5/1988 | Franses et al. | |
| 4,772,635 A | 9/1988 | Mitschker et al. | |
| 4,782,097 A | 11/1988 | Jain et al. | |
| 4,789,501 A | 12/1988 | Day et al. | |
| 4,793,980 A | 12/1988 | Torobin | |
| 4,795,741 A | 1/1989 | Leshchiner et al. | |
| 4,801,458 A | 1/1989 | Hidaka et al. | |
| 4,804,366 A | 2/1989 | Zdeb et al. | |
| 4,819,637 A | 4/1989 | Dormandy, Jr. et al. | |
| 4,822,535 A | 4/1989 | Ekman et al. | |
| 4,833,237 A | 5/1989 | Kawamura et al. | |
| 4,850,978 A | 7/1989 | Dudar et al. | |
| 4,859,711 A | 8/1989 | Jain et al. | |
| 4,863,972 A | 9/1989 | Itagaki et al. | |
| 4,897,255 A | 1/1990 | Fritzberg et al. | |
| 4,929,400 A | 5/1990 | Rembaum et al. | |
| 4,933,372 A | 6/1990 | Feibush et al. | |
| 4,938,967 A | 7/1990 | Newton et al. | |
| 4,946,899 A | 8/1990 | Kennedy et al. | |
| 4,954,399 A | 9/1990 | Tani et al. | |
| 4,981,625 A | 1/1991 | Rhim et al. | |
| 4,990,340 A | 2/1991 | Hidaka et al. | |
| 4,999,188 A | 3/1991 | Solodovnik et al. | |
| 5,007,940 A | 4/1991 | Berg | |
| 5,011,677 A | 4/1991 | Day et al. | |
| H915 H | 5/1991 | Gibbs | |
| 5,015,423 A | 5/1991 | Eguchi et al. | |
| 5,032,117 A | 7/1991 | Motta | |
| 5,034,324 A | 7/1991 | Shinozaki et al. | |
| 5,047,438 A | 9/1991 | Feibush et al. | |
| 5,079,274 A | 1/1992 | Schneider et al. | |
| 5,091,205 A | 2/1992 | Fan | |
| 5,106,903 A | 4/1992 | Vanderhoff et al. | |
| 5,114,421 A | 5/1992 | Polak | |
| 5,116,387 A | 5/1992 | Berg | |
| 5,120,349 A | 6/1992 | Stewart et al. | |
| 5,125,892 A | 6/1992 | Drudik | |
| 5,147,631 A | 9/1992 | Glajch et al. | |
| 5,147,937 A | 9/1992 | Frazza et al. | |
| 5,149,543 A | 9/1992 | Cohen et al. | |
| 5,158,573 A | 10/1992 | Berg | |
| 5,171,214 A | 12/1992 | Kolber et al. | |
| 5,171,217 A | 12/1992 | March et al. | |
| 5,181,921 A | 1/1993 | Makita et al. | |
| 5,190,760 A | 3/1993 | Baker | |
| 5,190,766 A | 3/1993 | Ishihara | |
| 5,192,301 A | 3/1993 | Kamiya et al. | |
| 5,202,352 A | 4/1993 | Okada et al. | |
| 5,216,096 A | 6/1993 | Hattori et al. | |
| 5,253,991 A | 10/1993 | Yokota et al. | |
| 5,260,002 A | 11/1993 | Wang | |
| 5,262,176 A | 11/1993 | Palmacci et al. | |
| 5,263,992 A | 11/1993 | Guire | |
| 5,288,763 A | 2/1994 | Li et al. | |
| 5,292,814 A | 3/1994 | Bayer et al. | |
| 5,302,369 A | 4/1994 | Day et al. | |
| 5,314,974 A | 5/1994 | Ito et al. | |
| 5,316,774 A | 5/1994 | Eury et al. | |
| RE34,640 E | 6/1994 | Kennedy et al. | |
| 5,320,639 A | 6/1994 | Rudnick | |
| 5,328,936 A | 7/1994 | Leifholtz et al. | |
| 5,336,263 A | 8/1994 | Ersek et al. | |
| 5,344,452 A | 9/1994 | Lemperle | |
| 5,344,867 A | 9/1994 | Morgan et al. | |
| 5,354,290 A | 10/1994 | Gross | |
| 5,369,133 A | 11/1994 | Ihm et al. | |
| 5,369,163 A | 11/1994 | Chiou et al. | |
| 5,382,260 A | 1/1995 | Dormandy, Jr. et al. | |
| 5,384,124 A | 1/1995 | Courteille et al. | |
| 5,397,303 A | 3/1995 | Sancoff et al. | |
| 5,398,851 A | 3/1995 | Sancoff et al. | |
| 5,403,870 A | 4/1995 | Gross | |
| 5,417,982 A | 5/1995 | Modi | |
| 5,431,174 A | 7/1995 | Knute | |
| 5,435,645 A | 7/1995 | Faccioli et al. | |
| 5,443,495 A | 8/1995 | Buscemi et al. | |
| 5,456,693 A | 10/1995 | Conston et al. | |
| 5,468,801 A | 11/1995 | Antonelli et al. | |
| 5,469,854 A | 11/1995 | Unger et al. | |
| 5,476,472 A | 12/1995 | Dormandy, Jr. et al. | |
| 5,484,584 A | 1/1996 | Wallace et al. | |
| 5,490,984 A | 2/1996 | Freed | |
| 5,494,682 A | 2/1996 | Cohen et al. | |
| 5,494,940 A | 2/1996 | Unger et al. | |
| 5,512,604 A | 4/1996 | Demopolis | |
| 5,514,090 A | 5/1996 | Kriesel et al. | |
| 5,525,334 A | 6/1996 | Ito et al. | |
| 5,534,589 A | 7/1996 | Hager et al. | |
| 5,541,031 A | 7/1996 | Yamashita et al. | |
| 5,542,935 A | 8/1996 | Unger et al. | |
| 5,553,741 A | 9/1996 | Sancoff et al. | |
| 5,556,391 A | 9/1996 | Cercone et al. | |
| 5,556,610 A | 9/1996 | Yan et al. | |
| 5,558,255 A | 9/1996 | Sancoff et al. | |
| 5,558,822 A | 9/1996 | Gitman et al. | |
| 5,558,856 A | 9/1996 | Klaveness et al. | |
| 5,559,266 A | 9/1996 | Klaveness et al. | |
| 5,567,415 A | 10/1996 | Porter | |
| 5,569,193 A | 10/1996 | Hofstetter et al. | |
| 5,569,449 A | 10/1996 | Klaveness et al. | |
| 5,569,468 A | 10/1996 | Modi | |
| 5,571,182 A | 11/1996 | Ersek et al. | |

| | | | | | |
|---|---|---|---|---|---|
| 5,580,575 A | 12/1996 | Unger et al. | 6,027,472 A | 2/2000 | Kriesel et al. |
| 5,583,162 A | 12/1996 | Li et al. | 6,028,066 A | 2/2000 | Unger |
| 5,585,112 A | 12/1996 | Unger et al. | 6,047,861 A | 4/2000 | Vidal et al. |
| 5,595,821 A | 1/1997 | Hager et al. | 6,048,908 A | 4/2000 | Kitagawa |
| 5,622,657 A | 4/1997 | Takada et al. | 6,051,247 A | 4/2000 | Hench et al. |
| 5,624,685 A | 4/1997 | Takahashi et al. | 6,056,721 A | 5/2000 | Shulze |
| 5,635,215 A | 6/1997 | Boschetti et al. | 6,056,844 A | 5/2000 | Guiles et al. |
| 5,637,087 A | 6/1997 | O'Neil et al. | 6,059,766 A | 5/2000 | Greff |
| 5,639,710 A | 6/1997 | Lo et al. | 6,063,068 A | 5/2000 | Fowles et al. |
| 5,648,095 A | 7/1997 | Illum et al. | 6,071,495 A | 6/2000 | Unger et al. |
| 5,648,100 A | 7/1997 | Boschetti et al. | 6,071,497 A | 6/2000 | Steiner et al. |
| 5,650,116 A | 7/1997 | Thompson | 6,073,759 A | 6/2000 | Lamborne et al. |
| 5,651,990 A | 7/1997 | Takada et al. | 6,090,925 A | 7/2000 | Woiszwillo et al. |
| 5,653,922 A | 8/1997 | Li et al. | 6,096,344 A | 8/2000 | Liu et al. |
| 5,657,756 A | 8/1997 | Vrba | 6,099,064 A | 8/2000 | Lund |
| 5,681,576 A | 10/1997 | Henry | 6,099,864 A | 8/2000 | Morrison et al. |
| 5,695,480 A | 12/1997 | Evans et al. | 6,100,306 A | 8/2000 | Li et al. |
| 5,695,740 A | 12/1997 | Porter | 6,139,963 A | 10/2000 | Fujii et al. |
| 5,698,271 A | 12/1997 | Liberti et al. | 6,149,623 A | 11/2000 | Reynolds |
| 5,701,899 A | 12/1997 | Porter | 6,160,084 A | 12/2000 | Langer et al. |
| 5,715,824 A | 2/1998 | Unger et al. | 6,162,377 A | 12/2000 | Ghosh et al. |
| 5,716,981 A | 2/1998 | Hunter et al. | 6,165,193 A | 12/2000 | Greene, Jr. et al. |
| 5,718,884 A | 2/1998 | Klaveness et al. | 6,179,817 B1 | 1/2001 | Zhong |
| 5,723,269 A | 3/1998 | Akagi et al. | 6,191,193 B1 | 2/2001 | Lee et al. |
| 5,725,534 A | 3/1998 | Rasmussen | 6,214,331 B1 | 4/2001 | Vanderhoff et al. |
| 5,733,925 A | 3/1998 | Kunz et al. | 6,214,384 B1 | 4/2001 | Pallado et al. |
| 5,741,331 A | 4/1998 | Pinchuk | 6,224,630 B1 | 5/2001 | Bao et al. |
| 5,746,734 A | 5/1998 | Dormandy, Jr. et al. | 6,224,794 B1 | 5/2001 | Amsden et al. |
| 5,752,974 A | 5/1998 | Rhee et al. | 6,235,224 B1 | 5/2001 | Mathiowitz et al. |
| 5,756,127 A | 5/1998 | Grisoni et al. | 6,238,403 B1 | 5/2001 | Greene, Jr. et al. |
| 5,760,097 A | 6/1998 | Li et al. | 6,245,090 B1 | 6/2001 | Gilson et al. |
| 5,766,147 A | 6/1998 | Sancoff et al. | 6,251,661 B1 | 6/2001 | Urabe et al. |
| 5,770,222 A | 6/1998 | Unger et al. | 6,258,338 B1 | 7/2001 | Gray |
| 5,779,668 A | 7/1998 | Grabenkort | 6,261,585 B1 | 7/2001 | Sefton et al. |
| 5,785,642 A | 7/1998 | Wallace et al. | 6,264,861 B1 | 7/2001 | Tavernier et al. |
| 5,785,682 A | 7/1998 | Grabenkort | 6,267,154 B1 | 7/2001 | Felicelli et al. |
| 5,792,478 A | 8/1998 | Lawin et al. | 6,268,053 B1 | 7/2001 | Woiszwillo et al. |
| 5,795,562 A | 8/1998 | Klaveness et al. | 6,277,392 B1 | 8/2001 | Klein |
| 5,797,953 A | 8/1998 | Tekulve | 6,280,457 B1 | 8/2001 | Wallace et al. |
| 5,807,323 A | 9/1998 | Kriesel et al. | 6,291,605 B1 | 9/2001 | Freeman et al. |
| 5,813,411 A | 9/1998 | Van Bladel et al. | 6,296,604 B1 | 10/2001 | Garibaldi et al. |
| 5,823,198 A | 10/1998 | Jones et al. | 6,296,622 B1 | 10/2001 | Kurz et al. |
| 5,827,502 A | 10/1998 | Klaveness et al. | 6,296,632 B1 | 10/2001 | Luscher et al. |
| 5,827,531 A | 10/1998 | Morrison et al. | 6,306,418 B1 | 10/2001 | Bley |
| 5,830,178 A | 11/1998 | Jones et al. | 6,306,419 B1 | 10/2001 | Vachon et al. |
| 5,833,361 A | 11/1998 | Funk | 6,306,425 B1 | 10/2001 | Tice et al. |
| 5,840,387 A | 11/1998 | Berlowitz-Tarrant et al. | 6,306,427 B1 | 10/2001 | Annonier et al. |
| 5,846,518 A | 12/1998 | Yan et al. | 6,312,407 B1 | 11/2001 | Zadno-Azizi et al. |
| 5,853,752 A | 12/1998 | Unger et al. | 6,312,942 B1 | 11/2001 | Pluss-Wenzinger et al. |
| 5,855,615 A | 1/1999 | Bley et al. | 6,315,709 B1 | 11/2001 | Garibaldi et al. |
| 5,863,957 A | 1/1999 | Li et al. | 6,335,384 B1 | 1/2002 | Evans et al. |
| 5,876,372 A | 3/1999 | Grabenkort et al. | 6,344,182 B1 | 2/2002 | Sutton et al. |
| 5,877,224 A | 3/1999 | Brocchini et al. | 6,355,275 B1 | 3/2002 | Klein |
| 5,885,216 A | 3/1999 | Evans, III et al. | 6,364,823 B1 | 4/2002 | Garibaldi et al. |
| 5,885,547 A | 3/1999 | Gray | 6,368,658 B1 | 4/2002 | Schwarz et al. |
| 5,888,546 A | 3/1999 | Ji et al. | 6,379,373 B1 | 4/2002 | Sawhney et al. |
| 5,888,930 A | 3/1999 | Smith et al. | 6,388,043 B1 | 5/2002 | Langer et al. |
| 5,891,155 A | 4/1999 | Irie | 6,394,965 B1 | 5/2002 | Klein |
| 5,894,022 A | 4/1999 | Ji et al. | 6,423,332 B1 | 7/2002 | Huxel et al. |
| 5,895,398 A | 4/1999 | Wensel et al. | 6,432,437 B1 | 8/2002 | Hubbard |
| 5,895,411 A | 4/1999 | Irie | 6,436,112 B2 | 8/2002 | Wensel et al. |
| 5,899,877 A | 5/1999 | Leibitzki et al. | 6,443,941 B1 | 9/2002 | Slepian et al. |
| 5,902,832 A | 5/1999 | Van Bladel et al. | 6,458,296 B1 | 10/2002 | Heinzen et al. |
| 5,902,834 A | 5/1999 | Porrvik | 6,476,069 B2 | 11/2002 | Krall et al. |
| 5,922,025 A | 7/1999 | Hubbard | 6,495,155 B1 | 12/2002 | Tice et al. |
| 5,922,304 A | 7/1999 | Unger | 6,544,503 B1 | 4/2003 | Vanderhoff et al. |
| 5,928,626 A | 7/1999 | Klaveness et al. | 6,544,544 B2 | 4/2003 | Hunter et al. |
| 5,935,553 A | 8/1999 | Unger et al. | 6,545,097 B2 | 4/2003 | Pinchuk et al. |
| 5,951,160 A | 9/1999 | Ronk | 6,575,896 B2 | 6/2003 | Silverman et al. |
| 5,957,848 A | 9/1999 | Sutton et al. | 6,602,261 B2 | 8/2003 | Greene, Jr. et al. |
| 5,959,073 A | 9/1999 | Schlameus et al. | 6,602,524 B2 | 8/2003 | Batich et al. |
| 6,003,566 A | 12/1999 | Thibault et al. | 6,605,111 B2 | 8/2003 | Bose et al. |
| 6,015,546 A | 1/2000 | Sutton et al. | 6,629,947 B1 | 10/2003 | Sahatjian et al. |

| | | | |
|---|---|---|---|
| 6,632,531 B2 | 10/2003 | Blankenship | |
| 6,652,883 B2 | 11/2003 | Goupil et al. | |
| 6,680,046 B1 | 1/2004 | Boschetti | |
| 6,699,222 B1 | 3/2004 | Jones et al. | |
| 7,131,664 B1 * | 11/2006 | Pang et al. | 280/743.2 |
| 2001/0001835 A1 | 5/2001 | Greene, Jr. et al. | |
| 2001/0016210 A1 | 8/2001 | Mathiowitz et al. | |
| 2001/0036451 A1 | 11/2001 | Goupil et al. | |
| 2001/0051670 A1 | 12/2001 | Goupil et al. | |
| 2002/0054912 A1 | 5/2002 | Kim et al. | |
| 2002/0061954 A1 | 5/2002 | Davis et al. | |
| 2002/0160109 A1 | 10/2002 | Yeo et al. | |
| 2002/0182190 A1 | 12/2002 | Naimark et al. | |
| 2002/0197208 A1 | 12/2002 | Ruys et al. | |
| 2003/0007928 A1 | 1/2003 | Gray | |
| 2003/0032935 A1 | 2/2003 | Damiano, Jr. et al. | |
| 2003/0108614 A1 | 6/2003 | Volkonsky et al. | |
| 2003/0183962 A1 | 10/2003 | Buiser et al. | |
| 2003/0185895 A1 | 10/2003 | Lanphere et al. | |
| 2003/0187320 A1 | 10/2003 | Freyman | |
| 2003/0194390 A1 | 10/2003 | Krall et al. | |
| 2003/0203985 A1 | 10/2003 | Baldwin et al. | |
| 2003/0206864 A1 | 11/2003 | Mangin | |
| 2003/0215519 A1 | 11/2003 | Schwarz et al. | |
| 2003/0233150 A1 | 12/2003 | Bourne et al. | |
| 2004/0091543 A1 | 5/2004 | Bell et al. | |
| 2004/0186377 A1 | 9/2004 | Zhong et al. | |
| 2005/0025800 A1 | 2/2005 | Tan | |
| 2005/0037047 A1 | 2/2005 | Song | |

FOREIGN PATENT DOCUMENTS

| | | |
|---|---|---|
| DE | 3834705 | 4/1990 |
| DE | 9414868.6 | 9/1994 |
| DE | 100 26 620 | 5/2000 |
| DE | 297 24 255 U1 | 10/2000 |
| EP | 0 067 459 A1 | 12/1982 |
| EP | 0 122 624 | 10/1984 |
| EP | 0 123 235 | 10/1984 |
| EP | 0 243 165 | 10/1987 |
| EP | 0 294 206 | 12/1988 |
| EP | 0 402 031 | 5/1990 |
| EP | 0 422 258 | 4/1991 |
| EP | 0 458 079 | 11/1991 |
| EP | 0 458 745 | 11/1991 |
| EP | 0 470 569 A1 | 2/1992 |
| EP | 0 547 530 B1 | 6/1993 |
| EP | 0 600 529 A | 12/1993 |
| EP | 0 623 012 B1 | 11/1994 |
| EP | 0 706 376 B1 | 4/1996 |
| EP | 0 730 847 A1 | 9/1996 |
| EP | 0 744 940 B1 | 12/1996 |
| EP | 0 797 988 A2 | 10/1997 |
| EP | 0 067 459 B1 | 3/1998 |
| EP | 0 764 047 | 8/2003 |
| EP | 0 993 337 | 4/2004 |
| ES | 2 096 521 | 3/1997 |
| JP | 59-196738 | 11/1884 |
| JP | 62-45637 | 2/1987 |
| JP | 4-74117 | 3/1992 |
| JP | 05-076598 | 3/1993 |
| JP | 6-57012 | 3/1994 |
| JP | 09-078494 | 3/1997 |
| JP | 9-110678 | 4/1997 |
| JP | 9-165328 | 6/1997 |
| JP | 9-316271 | 12/1997 |
| JP | 10-130329 | 5/1998 |
| JP | 04-057836 | 2/1999 |
| JP | 11-092568 | 4/1999 |
| JP | 2000189511 | 7/2000 |
| JP | 2001079011 | 3/2001 |
| JP | 2002 017848 | 1/2002 |
| JP | 2005-521520 | 7/2005 |
| NZ | 255409 | 2/1997 |
| NZ | 517377 | 8/2003 |
| TW | 421658 | 2/2001 |
| WO | WO 91/12823 | 5/1991 |
| WO | WO92/21327 | 12/1992 |
| WO | WO 93/00063 | 1/1993 |
| WO | WO93/19702 | 10/1993 |
| WO | WO94/10936 | 5/1994 |
| WO | WO95/03036 | 2/1995 |
| WO | WO95/22318 | 8/1995 |
| WO | WO 95/33553 | 12/1995 |
| WO | WO96/37165 | 11/1996 |
| WO | WO96/39464 | 12/1996 |
| WO | WO98/04616 | 2/1998 |
| WO | WO98/10798 | 3/1998 |
| WO | WO 98/26737 | 6/1998 |
| WO | WO98/47532 | 10/1998 |
| WO | WO 99/00187 | 1/1999 |
| WO | WO99/43380 | 2/1999 |
| WO | WO99/12577 | 3/1999 |
| WO | WO 99/51278 | 10/1999 |
| WO | WO99/57176 | 11/1999 |
| WO | WO 00/23054 | 4/2000 |
| WO | WO 00/032112 | 6/2000 |
| WO | WO 00/40259 | 7/2000 |
| WO | WO 00/71196 | 11/2000 |
| WO | WO 00/74633 A2 | 12/2000 |
| WO | WO 01/12359 | 2/2001 |
| WO | WO9804616 * | 2/2001 |
| WO | WO 01/66016 | 9/2001 |
| WO | WO 01/70291 A2 | 9/2001 |
| WO | WO 01/72281 | 10/2001 |
| WO | WO 01/76845 | 10/2001 |
| WO | WO 01/93920 | 12/2001 |
| WO | WO 02/11696 A2 | 2/2002 |
| WO | WO 02/34298 A1 | 5/2002 |
| WO | WO 02/34299 A1 | 5/2002 |
| WO | WO 02/34300 A1 | 5/2002 |
| WO | WO 02/43580 A2 | 6/2002 |
| WO | WO 03/016364 | 2/2003 |
| WO | WO 03/051451 | 6/2003 |
| WO | WO03/082359 | 9/2003 |
| WO | WO 2004/019999 * | 3/2004 |
| WO | WO 2004/020011 * | 3/2004 |
| WO | WO 2004/073688 | 9/2004 |
| WO | WO 2004/075989 | 9/2004 |

OTHER PUBLICATIONS

Bachtsi, A.R. et al., "An Experimental Investigation of Enzyme Release from Poly(vinyl alcohol) crosslinked Microspheres",*J. Microencapsulation*, vol. 12, No. 1, pp. 23-35; 1995.

Barr, J.D., et al.,"polyvinyl Alcohol Foam Particles Sizes and Concentrations Injectable through Microcatheters", *JVIR*, vol. 9, No. 1, pp. 113-118;1998.

Barttinnelli, L. et al., "New Class of Poly(vinyl alcohol) Polymrs as Column- Chromatography Stationary Phases for Candida Rugosa Lipase Isoforms Separation.",*J. Chromatogr A*, vol. 753, No. 1, pp. 47-55; 1996. Abstract. http://www.ncbi.nlm.nih.gov/entrez/query.fcgi?.

Berenstein, A. et al., "Catheter and Material Selection for Transarterial Embolization: Technical Considerations. II. Materials.",*Radiology*, vol. 132, No. 3, pp. 631-639; 1979.

Berenstein, A. et al., "Microembolization Techniques of Vascular Occlusion: Radiologic, Patohologic, and Clinical Correlation", *AJNR Am I Neuroradiol*, vol. 2, No. 3, pp. 261-267; 1981. Abstract. http://www.ncbi.nlm.nih.gov/entrez/query.fcgi?.

Bruix, J. et al., "Transarterial Embolization Versus Symptomatic Treatment in Patients With Advanced Hepatocellular Carcinoma: Results of a Randomized, Controlled Trial in a Single Institution", *Hepatology*, Jun. 1998, vol. 27, No. 6, pp. 1578-1583 Available Web Site: http://www.hepatitis-central.com/hcv/hcc/embolization/references.html.

Burczak, et al., "Long-term in vivo performance and biocompatibility of poly (vinyl alcohol) hydrogel macrocapsules for hybrid-type artificial pancreas",*Biomaterials*, vol. 17, No. 24, pp. 2351-2356, 1996, abs: http://www.ncbi.nlm.nih.gov/entrez/query.fcgi?cmd=retrieve&db=PubMed&list_uids=89824 . . . , pp. 1, 2002.

Burczak, et al., "Polymeric materials for biomedical purposes obtained by radiation methods. V. hybrid artificial pancreas", *Polim Med*, vol. 24, No. 1-2, pp. 45-55, 1994, abs: http://www.ncbi.nlm.nih.gov/entrez/query.fcgi?cmd=retrieve&db=PubMed&list_uids=7915 . . . , pp. 1, 2002.

Choe, et al., "An experimental study of embolic effect according to infusion rate and concentration of suspension in transarterial particulate embolization", *Invest Radiol*, vol. 32, No. 5, pp. 260-270, 1997, abs: http://www.ncbi.nlm.nih.gov/entrez/query.fcgi?cmd=retrieve&db=PubMed&list_uids=9140745&dopt+Abs . . . , pp. 1, 2002.

Colombo M, "Treatment of Hepatocellular Carcinoma", University of Milan, Inst Internal Med, Irccs Maggiore Res Unit Liver, Canc, Firc, Via Pace 9 1-20122 Milan, Italy Source: Journal of Viral Hepatitis, 1997;4:125-130 Available Web Site: http://home.texoma.net/~moreland/stats/hcc-9.html.

Derdeyn, et al., "Collagen-coated acrylic microspheres for embolotherapy: in vivo and in vitro characteristics", *American Journal of Neuroradiology*, vol. 18, No. 4, pp. 647-653, 1997, abs: http://www.ncbi.nlm.nih.gov/entrez/query.fcgi?cmd=retrieve&db=PubMed&list_uids=9127025&dopt=Abs . . . , pp. 1, 2002.

Derdeyn, et al., "Polyvinyl alcohol particle size and suspension characteristics",*American Journal of Neuroradiology*, vol. 16, pp. 1335-1343, 1995.

DiLuccio et al., "Sustained-Release Oral Delivery of Theophylline by Use of Polyvinyl Alcohol and Polyvinyl Alcohol-Methyl Acrylate Polymers",*Journal of Pharmaceutical Sciences*, Jan. 1994, vol. 83, No. 1, pp. 104-106.

Gander, et al., "Effect of polymeric network structure on drug release from cross-linked poly(vinyl alcohol) micromatrices", *Pharm Res, vol. 6, No. 7, pp. 578-584, 1989, abs: http://www.ncbi.nlm.nih.gov/entrez/query.fcgi?cmd=retrieve&db=PubMed&list_uids= 25080 . . . , pp. 1, 2002.*

Germano, et al., "Histopathological follow-up study of 66 cerebral arteriovenous malformations after therapeutic embolization with polyvinyl alcohol",*J Neurosurg*, vol. 76, No. 4, pp. 607-614, 1992, abs: http://www.ncbi.nlm.nih.gov/entrez/query.fcgi?cmd=retrieve&db=PubMed&list_uids=15452 . . . , pp. 1, 2002.

Geschwind et al., "Chemoembolization of Liver Tumor in a Rabbit Model: Assessment of Tumor Cell Death with Diffusion-Weighted MR Imaging and Histologic Analysis",*Journal of Vascular and Interventional Radiology*, Dec. 2000, vol. 11, No. 10, pp. 1244-1255.

Gohel, et al., "Formulation design and optimization of modified-release microspheres of diclofenac sodium", *Drug Dev Ind Pharm*, vol. 25, No. 2, pp. 247-251, 1999, abs: http://www.ncbi.nlm.nih.gov/entrez/query.fcgi?cmd=retrieve&db=PubMed&list_10065360&dop=A . . . , pp. 1, 2002.

Goodwin, et al., "Overview of embolic agents and their indications", *Eleventh Annual International Symposium on Endovascular Therapy*, pp. 303-306, 1999.

Grandfils, et al., "Preparation of poly (D,L) lactide microspheres by emulsion solvent evaporation, and their clinical implications as a convenient embolic material",*J Biomed Mater Res*, vol. 26, No. 4, pp. 467-479, 1992, abs: http://www.ncbi.nlm.nih.gov/entrez/query.fcgi?cmd=retrieve&db=PubMed&list_uids=1601900&dopt=Abs . . . , pp. 1, 2002.

Hamada, et al., "Embolization with cellulose porous beads, II: Clinical Trial", abs: http://www.ajnr.org/content/abstract/17/10/1901?ijkey=R.a2vRMietlXw, pp. 1-2, 2002.

Horak, et al., "Hydrogels in endovascular embolization. II. Clinical use of spherical particles", *Biomaterials*, vol. 7, 1986.

Huang, et al., "Percutaneous endovascular embolization of intracerebral arteriovenous malformations. Experience in 72 cases", *Chin Med J*, vol. 108, No. 6, pp. 413-419, 1995, abs: http://www.ncbi.nlm.nih.gov/entrez/query.fcgi?cmd=retrieve&db=PubMed&list_uids=75552 . . . , pp. 1, 2002.

Jack, et al., "Radiolabeled polyvinyl alcohol particles: a potential agent to monitor embolization procedures",*Int J Rad Appl Instrum B*, vol. 13, No. 3, pp. 235-243, 1986, abs: http://www.ncbi.nlm.nih.gov/entrez/query.fcgi?cmd=retrieve&db=PubMed&list_uids=37712, pp. 1, 2002.

Joy C, et al., 1991, "Use of Preoperative Embolization in the Treatment of Vascular Metastatic Lesions of the Spine" Available Web Site: http://www.aaos.org/wordhtml/anmeet91/scipro/ppr472.htm.

Kai, et al., "The utility of the microcrystalline cellulose sphere as a particulate embolic agent: an experimental study", *American Journal of Radiology*, vol. 21, No. 6, pp. 1160-1163, 2000, or http://www.ajnr.org/cgi/content/full/21/6/1160, pp. 1-7, 2002.

Kan, et al., "In vivo microscopy of the liver after injection of lipiodol into the hepatic artery and portal vein in the rat", *Acta Radiologica*, vol. 30, pp. 419-425, 1989.

Kerber et al., "Polyvinyl Alcohol Foam: Prepackaged Emboli for Therapeutic Embolization", *American Journal Roentgenol*, Jun. 1978, vol. 130, pp. 1193-1194.

Kerber, "Flow-Controlled Therapeutic Embolization: A Physiologic and Safe Technique", *AJR*, Mar. 1980, vol. 134, pp. 557-561.

Kim, et al., "Composite poly(vinyl alcohol) beads for controlled drug delivery", *Pharm Res*, vol. 9 No. 1, pp. 10-16, 1992, abs: http://www.ncbi.nlm.nih.gov/entrez/query.fcgi?cmd=retrieve&db=PubMed&list_uids=1589392&dopt=Abs . . . , pp. 1, 2002.

Kurata, et al., "Preoperative embolization for meningiomas using PVA particles", *No Shinkei Geka*, vol. 20, No. 4, pp. 367-373, 1992, abs: http://www.ncbi.nlm.nih.gov/entrez/query.fcgi?cmd=retrieve&db=PubMed&list_uids=1570057&dopt=Abs . . . , pp. 1, 2002.

Kurosaki et al., "Evaluation of PVA-Gel Spheres as GI-Transit Time Controlling Oral Drug Delivery System", *Proceedings of the 19th International Symposium on Controlled Release of Bioactive Materials*, Jul. 26-31, 1992, Orlando, Florida, pp. 273-274.

Kusano, et al., "Low-dose particulate polyvinylalcohol embolization in massive small artery intenstinal hemorrahage. Experimental and clinical results", *Invest Radiol*, vol. 22, No. 5, pp. 388-392, 1987, abs: http://www.ncbi.nlm.nih.gov/entrez/query.fcgi?cmd=retrieve&db=PubMed&list_uids=34963 . . . , pp. 1, 2002.

Labarre et al., "Complement activation by substituted polyacrylamide hydrogels for embolisation and implantation", *Biomaterials*, vol. 23, pp. 2319-2327, 2002.

Lammer, et al., "Transcatheral embolization with polyvinyl alcohol—technic and experimental studies", *Rontgenblatter*, vol. 36, No. 1, pp. 10-14, 1983, abs: http://www.ncbi.nlm.nih.gov/entrez/query.fcgi?cmd=retrieve&db=PubMed&list_uids=6823530&dop=Abs . . . , pp. 1, 2002.

Latchaw et al., "Polyvinyl foam embolization of Vascular and Neoplastic Lesions of the Head, Neck, and Spine", *Radiology*, Jun. 1979, vol. 131, pp. 669-679.

Leung et al., "Determinants of Postembolization Syndrome after Hepatic Chemoembolization", *Journal of Vascular and Interventional Radiology*, Mar. 2001, vol. 12, No. 3, pp. 320-326.

Markoff, et al., "Uterine arteriovenous malformation successfully embolized with a liquid polymer, isobutyl 2-cyanoacrylate", pp. 659-660, 1999.

Matsumaru, et al., "Embolic materials for endovascular treatment of cerebral lesions", *J Biomater Sci Polym Ed*, vol. 8, No. 7, pp. 555-569, 1997, abs: http://www.ncbi.nlm.nih.gov/entrez/query.fcgi?cmd=retrieve&db=PubMed&list_uids=91953 . . . , pp. 1, 2002.

Nakabayashi, et al., "Evaluation of particulate embolic materials with MR imaging, scanning electron microscopy, and phase-contrast microscopy", *American Journal of Neuroradiology*, vol. 18, No. 3, pp. 485-491, 1997, abs: http://www.ncbi.nlm.nih.gov/entrez/query.fcgi?cmd=retrieve&db=PubMed&list_uids=90904 . . . , pp. 1-2, 2002.

Nakstad, et al., "Embolization of intracranial arteriovenous malformations and fistulas with polyvinyl alcohol particles nad platinum fibre coils", *Neuroradiology*, vol. 34, No. 4, pp. 348-351, 1992, abs: http://www.ncbi.nlm.nih.gov/entrez/query.fcgi?cmd=retrieve&db=PubMed&list_uids=15284 . . . , pp. 1, 2002.

Nash, et al., "Modifications of polystyrenic matrices for the purification of proteins. II. Effect of the degree of glutaraldehyde-poly(vinyl alcohol) crosslinking on various dye ligand chromatography systems", *J Chromatogr A*, vol. 776, No. 1, pp. 55-63, 1997, abs: http://www.ncbi.nlm.nih.gov/entrez/query.fcgi?cmd=retrieve&db=PubMed&list_uids=92860 . . . , pp. 1, 2002.

Nikishin LF et al., 1999, "Interventional radiology in diffuse toxic goiter", *European congress of Radiology—ECR* 1999. Available Web Site: http://www.ecr.org/conferences/ecr1999/sciprg/abs/p090041.htm.

Ophir, et al., "Ultrasonic backscatter from contrast producing collagen microspheres", *Ultrasonic Imaging*, vol. 2, pp. 67-77, 1980.

Parker, et al., "A particulate contrast agent with potential for ultrasound imaging of liver", *Ultrasound in Medicine and Biology*, vol. 13, No. 9, pp. 555-566, 1987.

Pesant A.C. et al., 1997, "Dural fistulas involving the cavernous sinus: Treatment by embolization—cases", *European Congress of Radiology—ECR*1997. Available Web Site: http://www.ecr.org/conferences/ecr1997/sciprg/abs/9703088p.htm.

Pryor J and Berenstein A., "Epistaxis (Nose-bleeds)" Available Web Site: http://www.wehealny.org/inn/Radiology/nosebleeds.html, no date.

Purdy, et al., "Arteriovenous malformations of the brain: choosing embolic materials to enhance safety and ease of excision", *J Nerosurg*, vol. 77, No. 2, pp. 217-222, 1992, abs: http://www.ncbi.nlm.nih.gov/entrez/query.fcgi?cmd=retrieve&db=PubMed &list_uids=16250 . . . , pp. 1-2, 2002.

Quisling, et al., "Histopathology analysis of intraarterial polyvinyl alcohol microemboli in rat cerebral cortex", *American Journal of Neororadiology*, vol. 5, pp. 101-104, 1984.

Rajan et al., "Sarcomas Metastatic to the Liver: Response and Survial after Cisplatin, Doxorubicin, Mitomycin-C, Ethiodol, and Polyvinyl Alcohol Chemoembolization", *Journal of Vascular and Interventional Radiology*, Feb. 2001, vol. 12, no. 2, pp. 187-193.

Ramos, et al., "Tumor vascular signals in renal masses: detection with Doppler US", *Radiology*, vol. 168, No. 3, pp. 633-637, 1988.

Shafik, A., "Intraesophageal Polytef injection for the treatment of reflux esophagitis", *Department of Surgery and Experimental Research, Faculty of Medicine, Cairo University*, Cairo, Egypt, pp. 1-2, Received: Jun. 22, 1994; Accepted: Oct. 15, 1994 http://www.ahmedshafik.org/Group-D/d016.htm.

Spickler, et al., "The MR appearance of endovascular embolic agents in vitro with clinical correlation", *Comput Med Imaging Graph*, vol. 14, No. 6, pp. 415-423, 1990, abs: http://www.ncbi.nlm.nih.gov/entrez/query.fcgi?cmd=retrieve&db=PubMed&list_uids= 21487 . . . , pp. 1, 2002.

Strunk, et al., "Treatment of congenital coronary arteriovenous malformations with microparticle embolization", *Cathet Cardiovasc Diagn*, vol. 22, no. 2, pp. 133-136, 1991, abs: http://www.ncbi.nlm.nih.gov/entrez/query.fcgi?cmd=retrieve&db=PubMed &list_uids=2009563&dop=Abs . . . , pp. 1, 2002.

Swanson DA et al., 1980, "The role of embolization and nephrectomy in the treatment of metastatic renal carcinoma", Urologic Clinics of North America 7(3):719-730, 1980. University of Pennsylvania Cancer Center—Oncolink. Available Web Site: http://www.oncolink.upenn.edu/pdg_html/cites/00/00585.html.

Tabata et al., "Tumor accumulation of poly(vinyl alcohol) of different sizes after intravenous injection", *Journal of Controlled Release*, Jan. 2, 1998, vol. 50, Nos. 1-3, pp. 123-133.

Tadavarthy et al., "Polyvinyl Alcohol (Ivalon) as an Embolizing Agent", *The American Journal of Roentgenology Radium Therapy and Nuclear Medicine*, Nov. 1975, vol. 125, No. 3, pp. 609-616.

Tadavarthy et al., "Polyvinyl Alcohol (Ivalon) as an Embolizing Agent", *Seminars in Interventional Radiology*, vol. 1, No. 2, Department of Radiology, University of Minnesota Hospitals, Minneapolis, Minnesota, Jun. 1984, pp. 101-109.

Tao, et al., "Study of microspheres for embolization of the hepatic artery", *Yao Xue Xue Bao*, vol. 23, No. 1, pp. 55-60, 1988, abs: http://www.ncbi.nlm.nih.gov/entrez/query.fcgi?cmd=retrieve &db=PubMed&list_uids=3400477&dop=A, pp. 1, 2002.

Tao, et al., "Study on embolization of hepatitic artery using microspheres", Acta Pharmaceutica Sinica vol. 23, No. 1, pp. 55-60; 1988. Translation.

Terada, et al., "Preoperative embolization of meningiomas fed by ophthalmic branch arteries", *Surg Neurol*, vol. 45, No. 2, pp. 161-166, 1996, abs: http://www.ncbi.nlm.nih.gov/entrez/query.fcgi?cmd=retrieve&db=PubMed&list_uids=86070 . . . , pp. 1, 2002.

Thanoo, et al., "Controlled release of oral drugs from cross-linked polyvinyl alcohol microspheres", *J Pharm Pharmacol*, vol. 45, No. 1, pp. 16-20, 1993, abs: http://www.ncbi.nlm.nih.gov/entrez/query.fcgi?cmd=retrieve&db=PubMed&list_uids=8094438&dop= Abs . . . , pp. 1, 2002.

Thanoo, et al., "Tantalum loaded silicone microspheres as particulate emboli", *J Microencapsul*, vol. 8, No. 1, pp. 95-101, 1991, abs: http://www.ncbi.nlm.nih.gov/entrez/query.fcgi?cmd=retrieve &db=PubMed&list_uids=1880697&dop=Abs . . . , pp. 1, 2002.

Tikkakoski, et al., "Preoperative embolization in the management of neck paragangliomas", *Laryngoscope*, vol. 107, pp. 821-826, 1997.

Touho, et al., "Intravascular treatment of spinal arteriovenous malformations using a microcatheter—with special reference to serial xylocaine tests and intravascular pressure monitoring", *Surgical Neurology*, vol. 42, No. 2, pp. 148-156. 1994, abs: http://www.ncbi.nlm.nih.gov/entrez/query.fcgi?cmd=retrieve&db=PubMed &list_uids=80912 . . . , pp. 1, 2002.

Vivas S et al., "Arterioportal fistula and hemobilia in a patient with hepatic transplant", Gastroenterol Hepatol, Feb. 1998; 21(2):88-9. Available Web Site: http://www.doyma.es/copiani/revistas/gastro/abstr/abs_p080.html.

Wakhloo, et al., "Extended preoperative polyvinyl alcohol microembolization of intracranial meningiomas: Assessment of two embolization techniques", *American Journal of Neuroradiology*, vol. 14, pp. 571-582, 1993.

Walsh RM et al., 1998, "Role of Angiography and Embolization for Acute Massive Upper Gastronintestinal Hemorrhage." Department of General Surgery and Radiology, Cleveland Clinic Foundation, Cleveland, Ohio. Available Web Site: http://www.ssat.com/98ddw/abstscorrt-47.html.

Wikholm G et al., 1996, "Embolization of Cerebral Arteriovenous Malformations: Part I—Technique, Morphology, and Complications", Departments of Neurology (CL) and Interventional Radiology (GW, PS), Sahlgrenska University Hospital, Goteborg, Sweden. Neurosurgery. Sep. 1996;39(3):448-57; discussion 457-9. Available Web Site: http://www.wwilkins.com/neurosurgery/0148-396X9-96inter.html.

Worthington-Kirsch RL, 1999, "Interventionalists offer management option for uterine fibroids." Diagnostic Imaging, pp. 47-49. Available Web Site: http://www.dimag.com/references/9903wortrefs.html.

Worthington-Kirsch, et al., "Uterine arterial embolization for the management of leiomyomas: Quality-of-life assessment and clinical response", *Radiology*, vol. 208, No. 3, 625-629, 1998.

Yusi et al., "submuscosal Injection of Polyvinyl Alcohol in Artificially Created Vesico-Ureteral Reflux: A Preliminary Report," Asian J. Surg. 18(2): 122-127 (Apr. 1995).

Beaujeux, R. et al., "Trisacryl Gelatin Microspheres for Therapeutic Embolization, II: Preliminary Clinical Evaluation in Tumors and Arteriovenous Malformations," *AJNR Am. J. Neuroradiol.* 17:541-548, Mar. 1996.

Stridbeck, H. et al., "Collateral Circulation Following Repeated Distal Embolization of the Hepatic Artery in Pigs," *Invest Radiol* 1984;19:179-183.

Wright, K.C. et al., "Partial Splenic Embolization Using Polyvinyl Alcohol Foam, Dextran, Polystyrene, or Silicone," *Radiology* 142:351-354, Feb. 1982.

Markus, H.S., "Experimental Aspects of High-Intensity Transient Signals in the Detection of Emboli," *J Clin Ultrasound* 23:81-87 (1995).

Schwarz, K.Q., "The Acoustic Filter: An Ultrasonic Blood Filter for the Heart-Lung Machine," *Journal of Thoracic and Cardiovascular Surgery* 104(6):1647-1653 (1992).

Barton, P. et al., "Embolization of Bone Metastases", *Journal of Vascular and Interventional Radiology*, vol. 7, No. 1, Jan.-Feb. 1996, p. 81-88.

Jiaqi, Y. et al., "A New Embolic Material: Super Absorbent Polymer (SAP) Microsphere and Its Embolic Effects", *Nippon Acta Radiologica*1996 (56):19-24.

Mavligit, G. et al., "Gastrointestinal Leiomyosarcoma Metastic to the Liver", *Cancer*, vol. 75, No. 8, Apr. 15, 1995, pp. 2083-2088.

Thanoo, B. C. et al., "Preparation and Properties of Barium Sulphate and Methyl Iothalamate Loaded Poly(vinyl Alcohol) Microspheres as Radiopaque Particulate Emboli", *Journal of Applied Biomaterials*, vol. 2, 67-72 (1991).

Rump, A. et al., "Pharmacokinetics of Intraarterial Mitomycin C in the Chemoembolisation Treatment of Liver Metastases", *Gen. Pharmac.* vol. 27, No. 4, pp. 669-671, 1996.

Thanoo, B. C. et al., "Preparation and Properties of Barium Sulphate and Methyl Iothalamate Loaded Poly(vinyl Alcohol) Microspheres as Radiopaque Particulate Emboli", *Journal of Applied Biomaterials*, vol. 2, 67-72 (1991).

Wakhloo, A. et al., "Extended Preoperative Polyvinyl Alcohol Microembolization of Intracranial Meningiomas: Assessment of Two Embolization Techniques", *AJNR* 14, May-Jun. 1993, pp. 571-582.

Zou, Ying-hua, et al. "Experimental Canine Hapatic Artery Embolization with Polyvinyl Alcohol Microspheres", *Zhong Hua Fang-She Xue ZaZhi*, Dec. 23, 1989 (6):330-332.

Zou, Ying-hua, et al. "Experimental Canine Hapatic Artery Embolization with Polyvinyl Alcohol Microspheres" (Translation), *Zhong Hua Fang-She Xue ZaZhi*, Dec. 23, 1989 (6):330-332.

Abbara et al., "Transcervical Expulsion of a Fibroid as a Result of Uterine Artery Embolization for Leiomyomata", *JVIR*, vol. 10, No. 4, pp. 409-411, 1999.

Abrahams, J.M. et al., "Topic Review: Surface Modifications Enhancing Biological Activity of Guglielmi Detachable Coils in Treating Intracranial Aneurysms", *Surg. Neurol.* 54:34-41, 2000.

Abrahams, J.M. et al., "Delivery of Human Vascular Endothelial Growth Factor with Platinum Coils Enhances Wall Thickening and Coil Impregnation in a Rat Aneurysm Model", *AJNR Am. J. Neuroradiol.* 22:1410-1417, Aug. 2001.

Abuja, a.A., "Platinum Coil Coatings to Increase Thrombogenicity: a Preliminary Study in Rabbits", *AJNR Am. J. Neuroradiol.* 14:794-798; Jul./Aug. 1993.

Antibody Labeling, http://www.altcorp.com/AffinityLabeling/ablaeling.htm, pp. 1-6, May 20, 2003.

Berkowitz, R.P. et al., "Vaginal Expulsion of Submucosal Fibroids After Uterine Artery Embolization", *Journal of Reproductive Medicine*, vol. 44, No. 4, pp. 373-376; Apr. 1999 http://www.reproductivemedicine.com.

Bourke et al., "Protein Drug Release from Photocrosslinked Poly(vinyl alcohol) Hydrogels," *Society for Biomaterials 28th Annual Meeting Transactions*, p. 144 (2002).

Bradley, E.A. et al., "Transcatheter Uterine Artery Embolisation to Treat Large Uterine Fibroids", *British Journal of Obstetrics and Gynaecology*, vol. 105, pp. 235-240; Feb. 1998.

Brockmann, J. et al., "Radiolabeling of p-Bz-DOTA-CD-11c antibody with [88]Y: Conjugation, Labeling, Biodistribution studies", 2 pages, 2000 http://www.kernchemie.uni-mainz.de/downloads/jb2000/b14_ brockmann.pdf.

Buhle, Jr. EL, "Re: Re: Hepatic Arterial Embolization", *UCLA Medicine Online*, Mar. 10,1996, http://www.meds.com/archive/mol-cancer/1996/msg00128.html, 2 pages.

Capozza et al., "Endoscopic treatment of vesico-ureteric reflux and urinary incontinence: technical problems in the paediatric patient," *British Journal of Urology*, 75(4):538-542 (Apr. 1995).

Carroll, B.A. et al., "Microbubbles as Ultrasonic Contrast Agents", *Investigative Radiology*, vol. 14, No. 3, p. 374, Supplement to May-Jun. 1979.

Carroll, B.A. et al., "Gelatin Encapsulated Nitrogen Microbubbles as Ultrasonic Contrast Agents", *Journal of Clinical and Laboratory Research*, vol. 15, No. 1, pp. 260-266, Feb. 1980.

Carstensen, E.L. et al., "Determination of the Acoustic Properties of Blood and its Components", *Journal of Acoustical Society of America*, vol. 25, No. 2, pp. 286-289, Mar. 1953.

Chuang et al., "Experimental Canine Hepatic Artery Embolization with Polyvinyl Alcohol Foam Particles", *Departments of Diagnostic Radiology and Veterinary Medicine*, The University of Texas, M.D. Anderson Hospital and Tumor Institute at Houston, Texas, pp. 21-25, Oct. 1982.

Cirkel, U. et al., "Experience with Leuprorelin Acetate Depot in the Treatment of Fibroids: A German Multicentre Study", *Clinical Therapeutics*, vol. 14, Suppl. A, 1992.

Clarian Health Methodist — Indiana Lions Gamma Knife Center, "Arteriovenous Malformation," http://www.clarian.corn/tyhealth/gammaknife/cond_arter.asp, 4 pages, Last Updated on Mar. 20, 2000.

Concentric Medical, Inc.- Product Information (3 pages), 2002.

Cruise et al., "*In Vitro* and *In Vivo* Characterization of a Hydrogel-Based Aneurysm Embolization System," *Society for Biomaterials 28th Annual Meeting Transactions*, p. 203 (2002).

Deasy, P. B., "*Microencapsulation and Related Drug Processes*", New York, NY, Marcel Dekker, Inc., 345 pages, 1984 (Table of Contents only).

DeGast, A.N. et al., "Transforming Growth Factor β-coated Platinum Coils for Endovascular Treatment of Aneurysms: An Animal Study", *Neurosurgery*, vol. 49, No. 3, pp. 690-696, Sep. 2001.

Duckwiler et al., "Catheters, embolic agents spark neurointervention," *Diagnostic Imaging*, 16(5):66-72 (May 1994).

Ersek et al., "Bioplastique: A New Textured Copolymer Microparticle Promises Permanence in Soft-Tissue Augmentation," *Plastic and Reconstructive Surgery*, 87(4):693-702 (Apr. 1991).

Eskridge, "Interventional Neuroradiology," *Radiology*, 172:991-1006 (Nov. 1989).

Feldman, L. et al., "Transcatheter Vessel Occlusion: Angiographic Results Versus Clinical Success", *Radiology*, vol. 147, pp. 1-5, Apr. 1983.

Ferrofluids, Physical Properties and Applications Ferrofluidics Corp., Nashua, NH, 5 pages, 1986.

FeRx Incorporated, FERX Profile http://www.biotechshares.com/FERX.htm, 4 pages. (Retrieved from the internet on Jun. 26, 2003).

Fritzsch, T. et al., "SH U 508, A Transpulmonary Echocontrast Agent", *Investigative Radiology*, vol. 25, Supplement 1, pp. S160-S161, Sep. 1990.

Fujimoto, S. et al., "Biodegradable Mitomycin C Microspheres Given Intra-Arterially for Inoperable Hepatic Cancer", *Cancer*, vol. 56, pp. 2404-2410, 1985.

Gilbert, W.M. et al., "Angiographic Embolization in the Management of Hemorrhagic Complications of Pregnancy", *American Journal of Obstetrics and Gynecology*, vol. 166, No. 2, pp. 493-497, Feb. 1992.

Goldberg, B.B., "Ultrasonic Cholangiography", *Radiology*, vol. 118, pp. 401-404, Feb. 1976.

Goodwin, et al., "Preliminary experience with uterine artery embolization for uterine fibroids", *Journal of Vascular and Interventional Radiology*, vol. 8, No. 4, pp. 517-526, 1997.

Gramiak et al., "Echocardiography of the Aortic Root," *Investigative Radiology*, 3(5):356-366 (Sep.-Oct. 1968).

Gramiak R. et al., "Ultrasound Cardiography: Contrast Studies in Anatomy and Function", *Radiology*, vol. 92, No. 5, pp. 939-948, Apr. 1969.

Greenwood, L.H. et al., "Obstetric and Nonmalignant Gynecologic Bleeding: Treatment with Angiographic Embolization",*Radiology*, vol. 164, No. 1, pp. 155-159, Jul. 1987.

Gupta et al., "Plasma-induced graft polymerization of acrylic acid onto poly(ethylene terephthalate) films: characterization and human smooth muscle cell growth on grafted films," *Biomaterials*, 23:863-871 (2002).

Halstenberg et al., "Biologically Engineered Protein-graft-Poly(ethylene glycol) Hydrogels: A Cell Adhesive and Plasmin-Degradable Biosynthetic Material for Tissue Repair," *Biomacromolecules*, 3(4):710-723 (2002).

Hirano et al., "Transcutaneous Intrafold Injection For Unilateral Vocal Fold Paralysis: Functional Results," *Ann. Otol. Rhino Laryngol*, 99(8):598-604 (Aug. 1990).

Horak et al., "Hydrogels in endovascular embolization. I. Spherical particles of poly (2-hydroxyethyl methacrylate) and their medicobiological properties", *Biomaterials*, 7(3):188-192 (May 1986).

"Injectable Tissue Implant Could Repair Ravages of Surgery", Clemson University, Biotech Week, Oct. 22, 2003, p. 117.

Jones, S.K. et al., "Experimental Examination of a Targeted Hyperthermia System Using Inductively Heated Ferromagnetic Microspheres in Rabbit Kidney", *Phys. Med. Biol.*, vol. 46, No. 2, pp. 385- 398, Feb. 2001, www.iop.org/Journals/pb.

Jung et al., "Sulfobutylated poly(vinyl alcohol)-graft-poly(lactide-co-glycolide)s facilitate the preparation of small negatively charged biodegradable nanospheres," *Journal of Controlled Release*, 67:157-169 (2000).

Kallmes, D.F. et al., "In Vitro Proliferation and Adhesion of Basic Fibroblast Growth Factor- producing Fibroblasts on Platinum Coils", *Radiology*, vol. 206, No. 1, pp. 237-243, Jan. 1998.

Kerber, C., "Balloon Catheter with a Calibrated Leak", *Radiology*, vol. 120, pp. 547-550, Sep. 1976.

Khanlcan et al., "Embolic Effects of Superabsorbent Polymer Microspheres in Rabbit Renal Model: Comparison with Tris -acryl Gelatin Microspheres and Polyvinyl Alcohol," *Radiation Medicine*, 22(6):384-390 (20004).

Kim et al., "Poly(vinyl alcohol) beads with core-shell structure for drug delivery," Cosmetic and Pharmaceutical Applications of Polymers, Plenum Press, New York, pp. 209-214 (1991).

Kim et al., "Suspension polymerized poly(vinyl alcohol) beads for drug delivery," *Polymeric Materials: Science and Engineering. Proceedings of the ACS Division of Polymeric Materials: Science and Engineering*, 63:64-67 (1990).

Krinick et al., "A polymeric drug delivery system for the simultaneous delivery of drugs activatable by enzymes and/or light," *J. Biomater. Sci. Polymer Edn*, 5(4):303-324 (1994).

Kuhn, R et al., "Embolic Occlusion of the Blood Supply to Uterine Myomas: Report of 2 Cases",*Aust. NZ. J. Obstet. Gynaecol.*, vol. 39, No. 1, pp. 120-122, Feb. 1999.

Kurbatova, G.T. et al., "Magnetically-guided Anesthetics Based on Highly Dispersed Iron Powders Coated by Polyacrylamide", *Biofizika*, vol. 47, No. 2, pp. 331-337, Mar.-Apr. 2002 http://intapp.medscape.com/px/medlineapp.

Laurent, "Materials and biomaterials for interventional radiology," *Biomed. & Pharmacother.*, 52:76-88 (1998).

Lemperle et al., "PMMA Microspheres for Intradermal Implantation: Part I. Animal Research," *Annals of Plastic Surgery*, 26(1):56-63 (Jan. 1991).

Lendlein, A. et al., "Biodegradable, Elastic Shape-Memory Polymers for Potential Biomedical Applications", *Science*, vol. 296, pp. 1673-1676, May 31, 2002.

Leventon, William, "Hemocompatible Coatings for Blood-Contacting Devices", *Medical Device & Diagnostic Industry: Coating Technologies — New Methods to Ensure Blood Compatibility*, vol. 25, No. 8, pp. 62-67, Aug. 2003.

Levy et al., "Transcatheter Uterine Artery Embolization for the Treatment of Symptomatic Uterine Fibroid Tumors," *Journal of Women's Imaging*, 2(4):168-175 (2000).

Lipman, "Uterine artery embolization for the treatment of symptomatic uterine fibroids: A review," *Applied Radiology*, 29(7):15-20 (Jul. 2000).

Lowery, C.L. et al., "Screening Tests for Intrauterine Growth Retardation: A Comparison of Umbilical Artery Doppler to Real-Time Ultrasound", *Echocardiography*, vol. 7, No. 2, pp. 159-164, Mar. 1990.

Marich, K.W. et al., "Real-Time Imaging with a New Ultrasonic Camera: Part I, In Vitro Experimental Studies on Transmission Imaging of Biological Structures", *Journal of Clinical Ultrasound*, vol. 3, No. 1, pp. 5-16, Mar. 1975.

Maruhashi, "Modified Polyvinyl Alcohols I and II," *Polyvinyl Alcohol - Developments*, John Wiley & Sons, Chichester, England, pp. 160-161 and pp. 186-191 (1992).

Marx, W. F. et al., "Endovascular Treatment of Experimental Aneurysms by Use of Biologically Modified Embolic Devices: Coil-mediated Intraaneurysmal Delivery of Fibroblast Tissue Allografts", *AJNR. Am. J. Neuroradiol.*, vol. 22, pp. 323-333, Feb. 2001.

Matsumoto, H. et al., "Basic Fibroblast Growth Factor Released from a Platinum Coil with a Polyvinyl Alcohol Core Enhances Cellular Proliferation and Vascular Wall Thickness: An In Vitro and In Vivo Study", *Neurosurgery*, vol. 53, No. 2, pp. 402-408, Aug. 2003.

Matsumoto, Y. et al., "Room-Temperature Ferromagnetism in Transparent Transition Metal-Doped Titanium Dioxide", *Science*, vol. 291, pp. 854-856, Feb. 2, 2001 www.sciencemag.org.

McIvor, J. et al., "Pregnancy After Uterine Artery Embolization to Control Haemorrhage from Gestational Trophoblastic Tumour", *British Journal of Radiology*, vol. 69, No. 823, pp. 624-629, Jul. 1996.

Mid-America Interventional Radiological Society, "New Treatment for Uterine Fibroids Avoids Surgery," http://www.mirs.org/fibroids.htm, 6 pages, Submitted in Oct. 1999.

Moroz, P. et al., "Arterial Embolization Hyperthermia in Porcine Renal Tissue", *Journal of Surgical Research*, vol. 105, No. 2, pp. 209-214, Jun. 15, 2002.

Moroz, P. et al., "Hepatic Clearance of Arterially Infused Ferromagnetic Particles", *Int. J. Hyperthermia*, vol. 19, No. 1, pp. 23-24, Feb. 2003 Available web site: http://www.tandf.co.uk/joumals.

Namiki, "Application of Teflon Paste for Urinary Incontinence — Report of 2 Cases," *Uro. Int.*, 39:280-282 (1984).

Orienti et al., "Crosslinked Polyvinylalcohol Hydrogels as Vehicles for Hydrophilic Drugs," *Arch. Pharm. Pharm. Med. Chem.*, 333:421-424 (2000).

Orsini, L. F. et al., "Pelvic Organs in Premenarcheal Girls: Real-Time Ultrasonography", *Radiology*, vol. 153, No. 1, pp. 113-116, Oct. 1984.

Pedley et al., "Hydrogels in Biomedical Applications," *British Polymer Journal*, 12:99-110 (Sep. 1980).

Phillips, D. R. et al., "Experience with Laparoscopic Leiomyoma Coagulation and Concomitant Operative Hysteroscopy", *J. Am. Assoc. Gynecol. Laparosc*, vol. 4, No. 4, pp. 425-533, Aug. 1997.

Physicians' Desk Reference Family Guide to Women's Health, "Chapter 7 — Common Disorders of the Reproductive System," http://www.healthsquare.com/pdrfg/wh/chapters/wh1ch01.htm, 24 pages.

Pistel et al., "Brush-like branched biodegradable polyesters, part III Protein release from microspheres of poly(vinyl alcohol)-graft-poly(D,L-lactic-co-glycolic acid)," *Journal of Controlled Release*, 73:7-20(2001).

Politano et al., "Periurethral Teflon Injection for Urinary Incontinence," *The Journal of Urology*, 111:180-183(1974).

Poppe, W. et al., "Pregnancy after Transcatheter Embolization of a Uterine Arteriovenous Malformation", *Am. J. Obstet. Gynecol.*, vol. 156, No. 5, pp. 1179-1180, May 1987.

Pritchard, et al., "Poly(Vinyl Alcohol): Basic Properties and Uses", London, England: Gordon and Breach Science Publishers, pp. 95-97, 1970.

Progelhof et al., "Table 4.21. Properties of electrical insulating films (101)," *Polymer Egineering Principles: Properties, Processes, and Tests for Design*, Hanser Publishers, Munich, p. 383 (1993).

PVA Plus, AngioDynamics® Inc., "Reliable PVA Foam Formulated for Consistency and Controlled Delivery — Embolization Particles Ordering Information," www.angiodynamics.com, 2 pages (Aug. 2002).

Ravina, J.H. et al., "Advantage of Pre-Operative Embolization of Fibroids: About a Multicentric Set of 31 Cases", *Contracept. Fertil. Sex.*, vol. 23, No. 1, pp. 45-49, Jan. 1995 (abstract).

Ravina, J.H. et al., "Arterial Embolisation to Treat Uterine Myomata", *Lancet* vol. 346, pp. 671- 674, Sep. 9, 1995.

Ravina, J.H. et al., "Interest of Particulate Arterial Embolization in the Treatment of Some Uterine Myoma", *Bull. Acad. Natle. Med.*, vol. 181, No. 2, pp. 233-246, Feb. 4, 1997 (Summary).

Rhine et al., "Polymers for Sustained Macromolecule Release: Procedures to Fabricate Reproducible Delivery Systems and Control Release Kinetics," *Journal of Pharmaceutical Sciences*, 69(3):265-270 (Mar. 1980).

Schlief, R. et al., "Enhanced Color Doppler Echocardiography of the Left Heart After Intravenous Injection of a New Saccharide Based Agent in Humans", *Circulation*, vol. 82, No. 2, p. 28, Oct. 1990 (Abstract).

Schlief, R. et al., "Successful Opacification of the Left Heart Chamber on Echocardiographic Examination after Intravenous Injection of a New Saccharide Based Contrast Agent", *Echocardiography*, vol. 7, No. 1, pp. 61-64, Jan. 1990.

Shafik, "Intraesophageal Polytef injection for the treatment of reflux esophagitis," *Surg. Endosc.*, 10:329-331 (1996).

Schetky, "Shape-Memory Alloys," *Encyclopedia of Chemical Technology*, Third Edition, vol. 20, John Wiley & Sons, New York, pp. 726-736 (1982).

Shung, K.K. et al., "Scattering of Ultrasound by Blood", *IEEE Transactions on Biomedical Engineering*, vol. BME-23, No. 6, pp. 460-467, Nov. 1976.

Sigelmann, R.A. et al., "Analysis and Measurement of Ultrasound Backscattering from an Ensemble of Scatters Excited by Sine-Wave Bursts", *Journal of Acoustical Society of America*, vol. 53, No. 4, pp. 1351-1355, Apr. 1973.

SIR-Spheres, Radioactive Implant (Yttrium-90 Microspheres), Sirex Medical, Inc., San Diego, CA, Nov. 6, 2000, pp. 1-15.

Sirtex Medical Limited — Product Description http://www.sirtex.com/?p=72, 3 pages (Retrieved from the internet on May 27, 2003).

Sirtex Medical Limited — Targeted Radiotherapy with SIR-Spheres http://www.sirtex.com/?p=57, 2 pages (Retrieved from the internet on May 27, 2003).

Siskin et al., "Pathologic Evaluation of a Spherical Polyvinyl Alcohol Embolic Agent in a Porcine Renal Model," *J. Vasc. Interv. Radiol.*, 14:89-98 (2003).

Skotland, T. et al., "In Vitro Stability Analyses as a Model for Metabolism of Ferromagnetic Particles (Clariscan™), a Contrast Agent for Magnetic Resonance Imaging", *J. Pharm. Biomed. Anal.*, vol. 28, No. 2, pp. 323-329, Apr. 15, 2002.

"Smart Sutures Tie Themselves", Apr. 26, 2002, http://www.sciam.com/article.cfm?articleID=00047706-121F-ICD0-B4A8809EC588, 2 pages.

Smith et al., "Evaluation of Polydimethylsiloxane as an alternative in the Endoscopic Treatment of Vesicoureteral Reflux," *The Journal of Urology*, 152:1221-1224 (Oct. 1994).

Smith, M.D. et al., "Left Heart Opacification with Peripheral Venous Injection of a New Saccharide Echo Contrast Agent in Dogs", *JACC*, vol. 13, No. 7, pp. 1622-1628, Jun. 1989.

Soppimath et al., "Controlled release of antihypertensive drug from the interpenetrating network poly(vinyl alcohol)-guar gum hydrogel microspheres," *J. Biomater. Sci. Polymer Edn.*, 11(1):27-43 (2000).

Spies JB, "Georgetown University Medical Center. Uterine Fibroid Embolization (UFE). An alternative to surgery for patients with uterine fibroids. Literature Review," http://www.fibroidoptions.com/pr-lit.htm, 6 pages, Sep. 1, 2001.

Stancato-Pasik, A. et al., "Obstetric Embolotherapy: Effect on Menses and Pregnancy", *Radiology*, vol. 204, No. 3, pp. 791-793, Sep. 1997.

Stein, R. et al., "Targeting Human Cancer Xenografts with Monoclonal Antibodies Labeled Using Radioiodinated, Diethylenetriaminepentaacetic Acid-appended Peptides", *Clinical Cancer Research*, vol. 5, No. 10, pp. 3079-3087, Oct. 1999 (Supplement).

Strasnick et al., "Transcutaneous Teflon® Injection for Unilateral Vocal Cord Paralysis: An Update," *The Laryngoscope*, 101:785-787 (Jul. 1991).

Tamatani, S. et al., "Histological Interaction of Cultured Endothelial Cells and Endovascular Embolic Materials Coated with Extracellular Matrix", *J. Neurosurg.*, vol. 86, No. 1, pp. 109-112, Jan. 1997.

Thelen, V.M. et al., "Catheter Embolisation of Metastasising Renal Carcinomas Using Butyle-2- cyano-acrylate", *Fortschr. Rontgenstr.*, vol. 124, No. 3, pp. 232-235, Mar. 1976.

Tian et al., "Design and synthesis of amphiphilic poly (ethylene glycol) derivatives as micellar drug delivery systems," *Polymer Preprints*, 43(2):719-720 (Fall 2002).

Toon, "Improving a Key Weapon Against Cancer," Research Horizons, pp. 11-12, Spring/Summer 2001.

University Medical Center SUNY Stony Brook, Department of Urology, "Variococele and its treatment," http://www.hsc.sunysb.edu/urology/male_inf. . . varicoele_and _its_treatment.html, 8 pages, Last Updated on Mar. 12, 2001.

Walker Wj, "Non Surgical Treatment of Fibroids in the UK by Uterine Artery Embolisation - An Alternative to Hysterectomy, Myomectomy and Myolysis," http://www.fibroids.co.uk/theoaper.html, 2002.

Waltman, a.C. et al., "Technique for Left Gastric Artery Catheterization", *Radiology*, vol. 109, No. 3, pp. 732-734, Dec. 1973.

White, Jr., "Embolotherapy in Vascular Disease," *American Journal of Roentgenology*, 142:27-30 (Jan. 1984).

Widder, K.J. et al., "Selective Targeting of Magnetic Microspheres Containing Adriamycin: Total Remission in Yoshida Sarcoma-Bearing Rats", *Proceedings of the le Annual Meeting of American Society of Clinical Oncology*, May 26-27, 1980, San Diego, CA, p. 261.

Widder, K. et al., "Magnetic Microspheres: Synthesis of a Novel Parenteral Drug Carrier", *Journal of Phannaceutical Sciences*, vol. 68, No. 1, pp. 79-82, Jan. 1979.

Winters et al., "Periurethral injection of collagen in the treatment of intrinsic sphincteric deficiency in the female patient," *The Urologic Clinics of North America*, 22(3):673-678 (Aug. 1995).

Wu, A.M., "Engineered Antibodies for Breast Cancer Imaging and Therapy," http://www.cbcrp.org/research/PageGrant.asp?grant_id=111, 3 pages, 1996.

Yamada, T. et al., "Extended Intraarterial Cisplatin Infusion for Treatment of Gynecologic Cancer After Altercation of Intrapelvic Blood Flow and Implantation of a Vascular Access Device", *Cardiovasc. Intervent. Radiol.*, vol. 19, pp. 139-145, 1996.

Yamashita, Y. et al., "Transcatheter Arterial Embolization of Obstetric and Gynaecological Bleeding: Efficacy and Clinical Outcome", *British Journal of Radiology*, vol. 67, pp. 530-534, Jun. 1994.

Yoon et al., "Surface Immobilization of Galactose onto Aliphatic Biodegradable Polymers for Hepatocyte Culture," *Biotechnol Bioeng.*, 78(1):1-10 (Apr. 5, 2002).

Zisch et al., "Covalently conjugated VEGF-fibrin matrices for endothelialization," *Journal of Controlled Release*, 72:101-113(2001).

Ziskin, M.C. et al., "Contrast Agents for Diagnostic Ultrasound", *Investigative Radiology*, vol. 7, No. 6, pp. 500-505, Nov.-Dec. 1972.

Kim et al., "Hollow Silica Spheres of Controlled Size and Porosity by Sol-Gel Processing," *J. Am. Ceram. Soc.*, 74(8):1987-1992 (Aug. 1991).

MerocelXL Sponge with Hytrol http://www.xomed.com/newproducts/merocelx1/merocelx1_earwick.asp, 3 pages, 2001.

Shape Shifters, http://www.sciam.com/tehbiz/0501scicit6.html, 3 pages, 2001.

The Vanderbilt-Ingram Cancer Center, "Kidney Cancer," http://www.mc.Vanderbilt.Edu/cancer/cancerinfo/kidney.html, 1 page, 2001.

* cited by examiner

EMBOLIZATION

This application is a continuation-in-part (and claims the benefit of priority under 35 U.S.C. § 120) of U.S. application Ser. No. 10/109,966, entitled "Processes for Manufacturing Polymeric Microspheres", filed Mar. 29, 2002, hereby incorporated by reference in its entirety.

TECHNICAL FIELD

This invention relates to embolization.

BACKGROUND

Therapeutic vascular occlusions (embolizations) are used to prevent or treat pathological conditions in situ. Compositions including embolic particles are used for occluding vessels in a variety of medical applications. Delivery of embolic particles through a catheter is dependent on size uniformity, density and compressibility of the embolic particles.

SUMMARY

In a first aspect, the invention features an embolic composition. The composition includes substantially spherical embolic particles having a diameter of about 1200 micron or less. The particles include polyvinyl alcohol and an interior having relatively large pores and a surface region with fewer relatively large pores.

In another aspect, the invention features an embolic composition including embolic polymer particles having a diameter of about 1200 micron or less and a surface with a predominant pore size of about 2 micron or less and pores interior to surface of about 10 micron or more.

In another aspect, the invention features an embolic composition including embolic polymer particles including a surface region from about 0.8r to r, the predominant pore size in the surface region being smaller than the predominant pore size in a region C to 0.3r.

In another aspect, the invention features an embolic composition, including embolic particles with a surface region defined primarily by relatively small pores and an interior region defined primarily of relatively large pores.

In another aspect, the invention features a method of manufacturing embolic particles. The method includes generating drops of a base polymer and a gelling compound and combining the particles with a pharmaceutically acceptable medium. The method may optionally include reacting the base polymer and removing the gelling compound. In another aspect, the invention features forming embolic particles by nebulization such as vibratory nebulization.

In another aspect, the invention features embolic compositions including particles formed by the processes described herein.

In another aspect, the invention features a method of delivering a therapeutic agent to a patient. The method includes administering to a patient in need of an embolization a therapeutically effective amount of substantially spherical embolic polymer particles. The particles include polyvinyl alcohol and include an interior region having relatively large pores and a surface region having fewer relatively large pores.

Embodiments may also include one or more of the following. The relatively large pores are about 20 or 30 micron or more. The surface region is about r to 0.8r. The surface region is about r to 2r/3. The particles include a body region from about 2r/3 to r/3 including intermediate size pores and the body region has more intermediate size pores than the surface region. The center region is from about r/3 to 3, the outer region including large size pores and the body region has fewer large size pores than the center region. The intermediate size pores are about 2 to 18 microns. The surface region is substantially free of pores greater than about 5 microns.

Embodiments may also include one of the following. The predominant pore size progressively increases from surface to the center of the particle. The predominant pore size on the particle surface is about 1 micron or less. The particles have a surface region from about (2r)/3 to the surface wherein the predominant pore size is in the range of about 1 micron or less. The predominant pore size is about 0.1 micron or less. Interior of said surface region, the particles have a predominant pore size in the range of about 2 to 35 microns. The particles include a center region from about C to r/3 in which the predominant pore size is about 20 to 35 microns. The particles have a body region from r/3 to (2r)/3 in which the predominant pore size is about 2 to 18 microns. The particles have a surface region from about (2r)/3 to the periphery and the predominant pore size in the surface region is about 10% or less than the predominant pore size in the interior to the surface region. The particles include a surface region from about 0.8r to r wherein the predominate pore size is about 1 micron or less. The particles include a region from about C to 0.8r includes pores having a diameter of 10 microns or more. The region C to 0.8r has a predominant pore size of about 3.5 to 2 microns. The particles have a density of about 1.1 to about 1.4 g/cm$^3$. The particles have a density of about 1.2 to 1.3 g/cm$^3$. The embolic particles have a sphericity of about 90% or more. The particles have an initial sphericity of about 97% or more. The particles have a sphericity of about 0.90 after compression to about 50%. The particles have a size uniformity of about +15% or more.

Embodiments may also include one or more of the following. The particles include about 1% or less polysaccharide. The polysaccharide is alginate. The alginate has a guluronic acid content of about 60% or greater. The embolic particles are substantially insoluble in DMSO. The embolic particles are substantially free of animal-derived compounds. The polyvinyl alcohol is composed of substantially unmodified polyvinyl alcohol prepolymer. The polyvinyl alcohol is predominantly intrachain 1,3-diols acetalized. The composition includes saline and/or contrast agent. The particles and/or composition are sterilized.

Embodiments may also include one or more of the following. The gelling compound is a polysaccharide The gelling compound is alginate. The alginate has a guluronic acid content of about 60% or more. The drops are contacted with a gelling agent. The gelling agent is a divalent cation. The cation is Ca+2. The base polymer is PVA. The PVA is reacted by acetalization. The PVA has a molecular weight of about 75,000 g/mole or greater. The viscosity of the base polymer and gelling compound is modified prior to forming said drops. The viscosity is modified by heating. The drops are formed by vibratory nebulization.

Embodiments may also include one or more of the following. Administration is by percutaneous injection. Administration is by a catheter. The particles are introduced to the body through a lumen, and the lumen has a smaller diameter than the particles. The composition is used for treatment of uterine fibroids. The composition is used for treatment of tumors, including hypervascular tumors and for arteriovenous malformations (AVMs).

Embodiments of the invention may have one or more of the following advantages. Some disorders or physiological conditions can be mediated by delivery of embolic compositions. Embolic compositions can be used, for example, in treatment of fibroids, internal bleeding AVMs and hypervascular tumors. Fibroids can include uterine fibroids which grow within the uterine wall, on the outside of the uterus, inside the uterine cavity, between the layers of broad ligament supporting the uterus, attached to another organ or on a mushroom-like stalk. Internal bleeding includes gastrointestinal, urinary, renal and varicose bleeding. AVMs are, for example, abnormal collections of blood vessels which shunt blood from a high pressure artery to a low pressure vein, resulting in hypoxia and malnutrition of those regions from which the blood is diverted.

Spherical embolic particles in the embolic compositions can be tailored to a particular application by varying particle size, porosity gradient, compressibility, sphericity and density of the particles. The uniform size of the spherical embolic particles can, for example, fit through the aperture of a catheter for administration by injection to a target site without partially or completely plugging the lumen of the catheter. The spherical embolic particles have a diameter of about 1200 micron or less. Size uniformity of ±15% of the spherical embolic particles allows the particles to stack evenly in the cylindrical lumen of the blood vessel to completely occlude the blood vessel lumen. Suspensions containing the embolic particles at density of about 1.1 to about 1.4 g/cm$^3$ can be prepared in calibrated concentrations of the embolic particles for ease of delivery by the physician without rapid settlement of the suspension. Control in sphericity and uniformity of the embolic particles can result in reduction in aggregation caused, for example, by surface interaction of the particles. In addition, the embolic particles are relatively inert in nature.

The details of one or more embodiments of the invention are set forth in the accompanying drawings and the description below. Other features, objects, and advantages of the invention will be apparent from the description and drawings, and from the claims.

BRIEF DESCRIPTION OF THE DRAWINGS

FIG. 1A is a schematic illustrating injection of an embolic composition including embolic particles into a vessel, while

FIG. 2A is a light micrograph of a collection of hydrated embolic particles, while

FIG. 3A is a schematic of the manufacture of an embolic composition while

Like reference symbols in the various drawings indicate like elements.

DETAILED DESCRIPTION

Composition

Figure 1A:
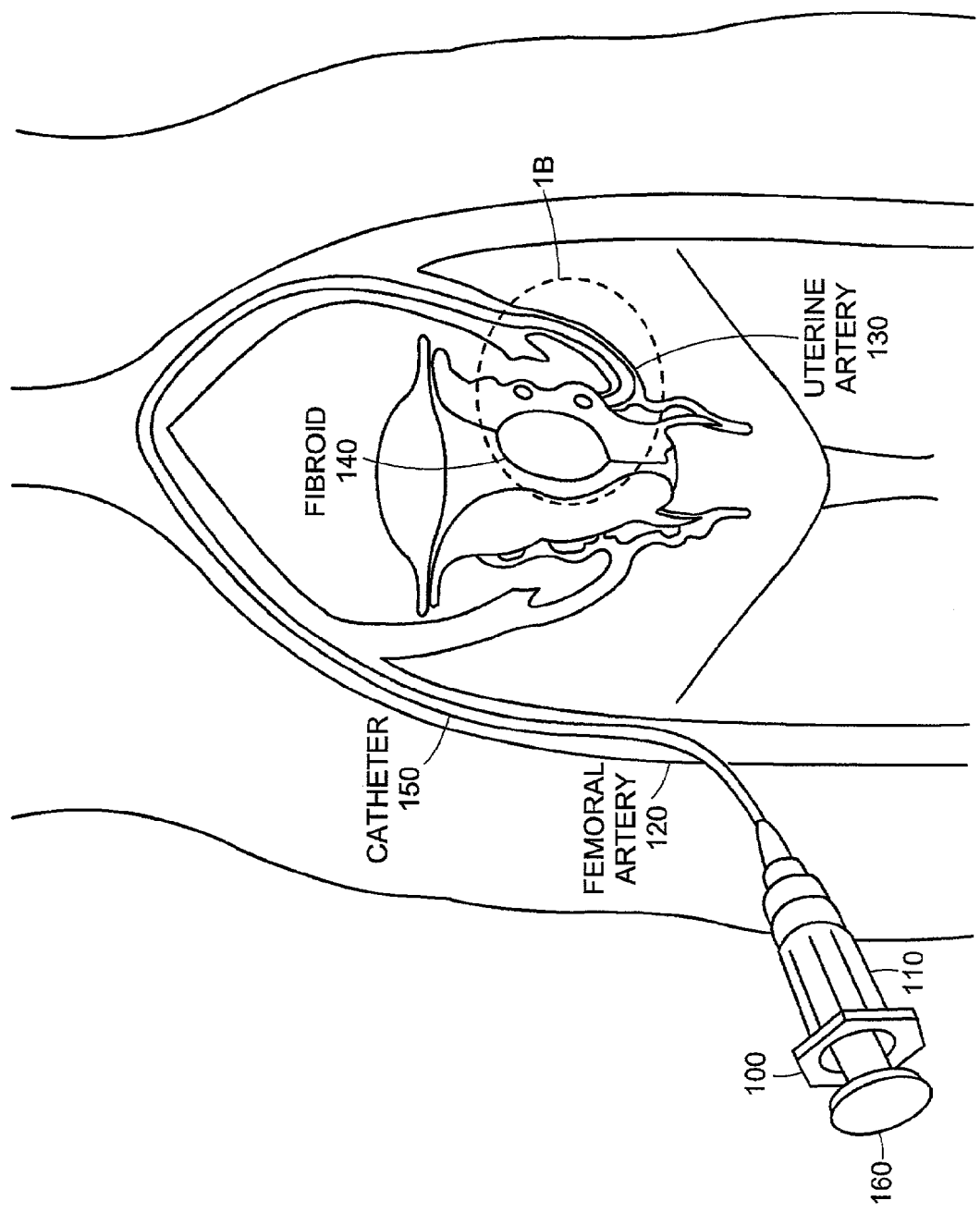
Figure 1B:
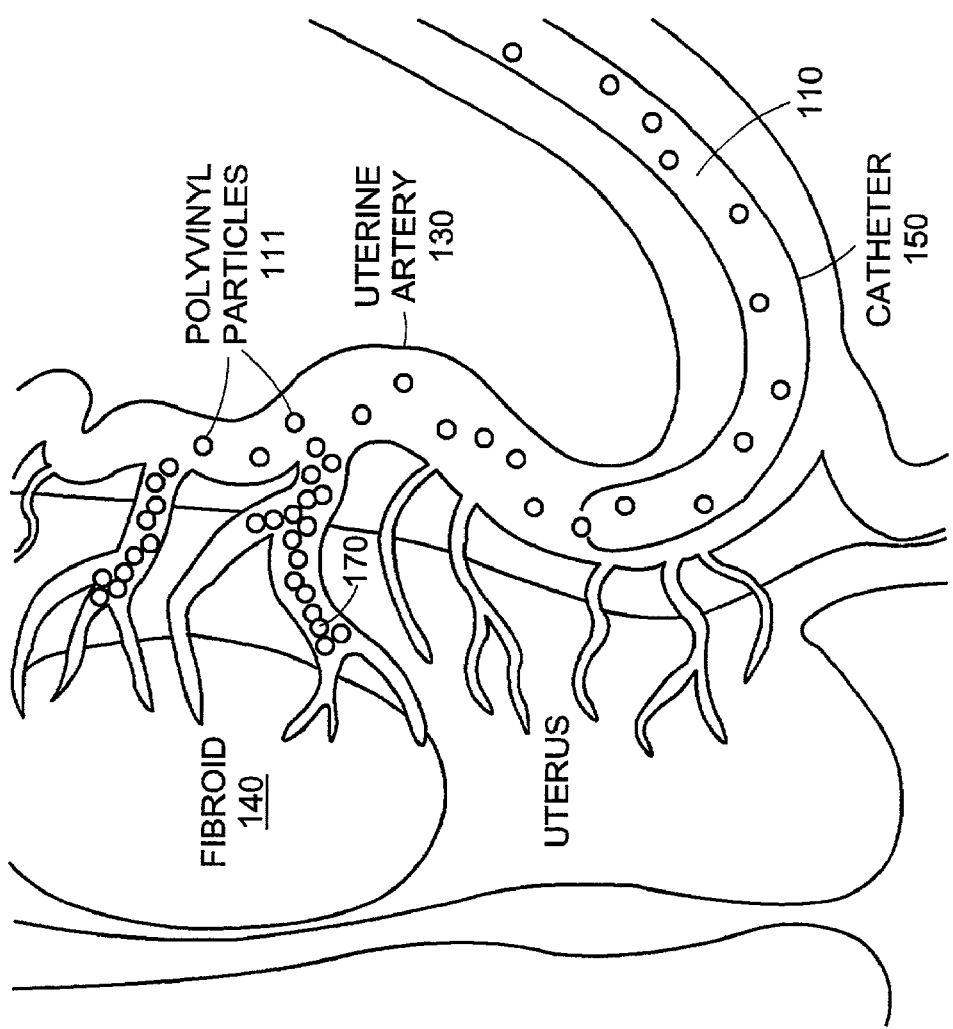
FIG. 1B is a greatly enlarged view of the region A in FIG. 1A.

Referring to FIGS. 1A and 1B, an embolic composition 100, including embolic particles 111 and carrier fluid, is injected into a vessel through an instrument such as a catheter 150. The catheter is connected to a syringe barrel 110 with a plunger 160. The catheter 150 is inserted, for example, at the leg of a patient into a femoral artery 120 to deliver the embolic composition 100 to, for example, occlude a uterine artery 130 leading to a fibroid 140. The fibroid 140 is located in the uterus of a female patient. The embolic composition 100 is initially loaded into the syringe 110. The plunger 160 of syringe 110 is compressed to deliver the embolic composition 100 through the catheter into lumen of the uterine artery 130.

Referring particularly to FIG. 1B which is an enlarged view of section A of FIG. 1A, the uterine artery 130 is subdivided into smaller uterine vessels 170 (about 2 mm or less) which feed a uterine fibroid 180. The embolic particles 111 in embolic composition 100 partially or totally fill the lumen of uterine artery 130, either partially or completely occluding the lumen of the uterine artery 130 feeding the uterine fibroid 140.

The particles are substantially formed of polymer such as a highly water insoluble, high molecular weight polymer. As will be discussed below, a preferred polymer is high molecular weight polyvinyl alcohol (PVA) that has been acetalized. Preferably, the embolic particles are substantially pure intra-chain 1,3 acetalized PVA and substantially free of animal derived residue such as collagen. In embodiments, the particles include a minor amount, e.g. less than about 0.2 weight %, of alginate or another polysaccharide or gelling material.

Figure 2A:
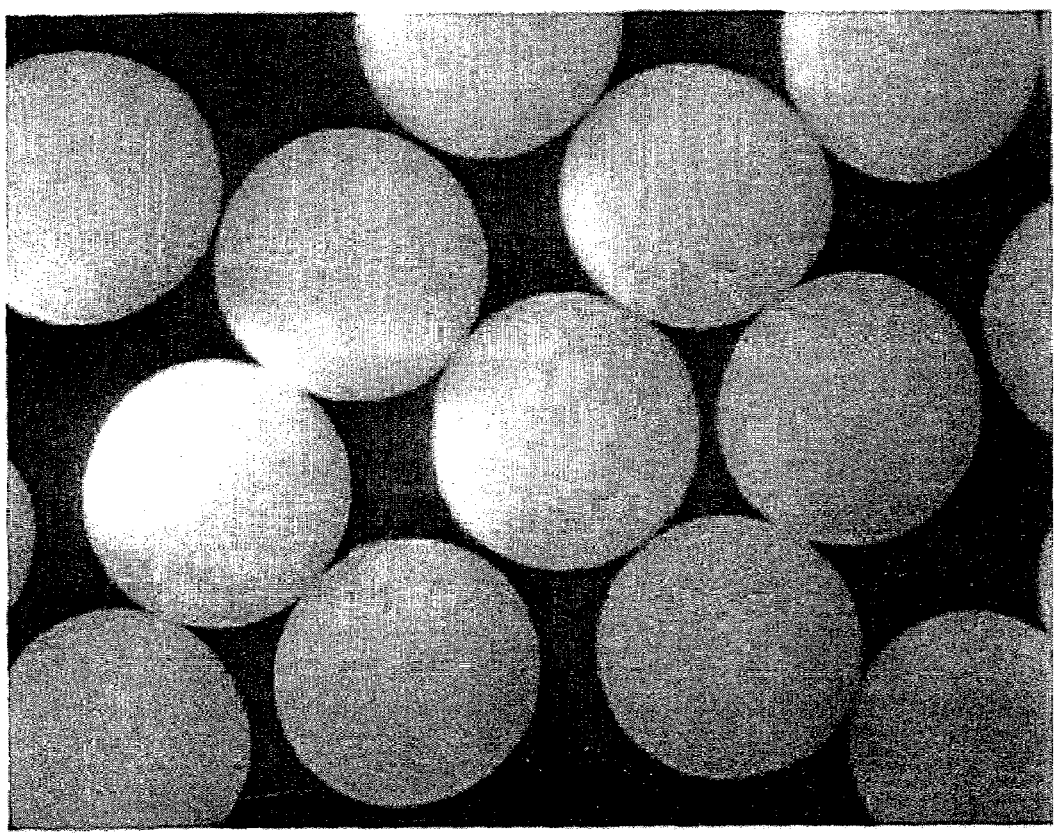
Figure 2B:
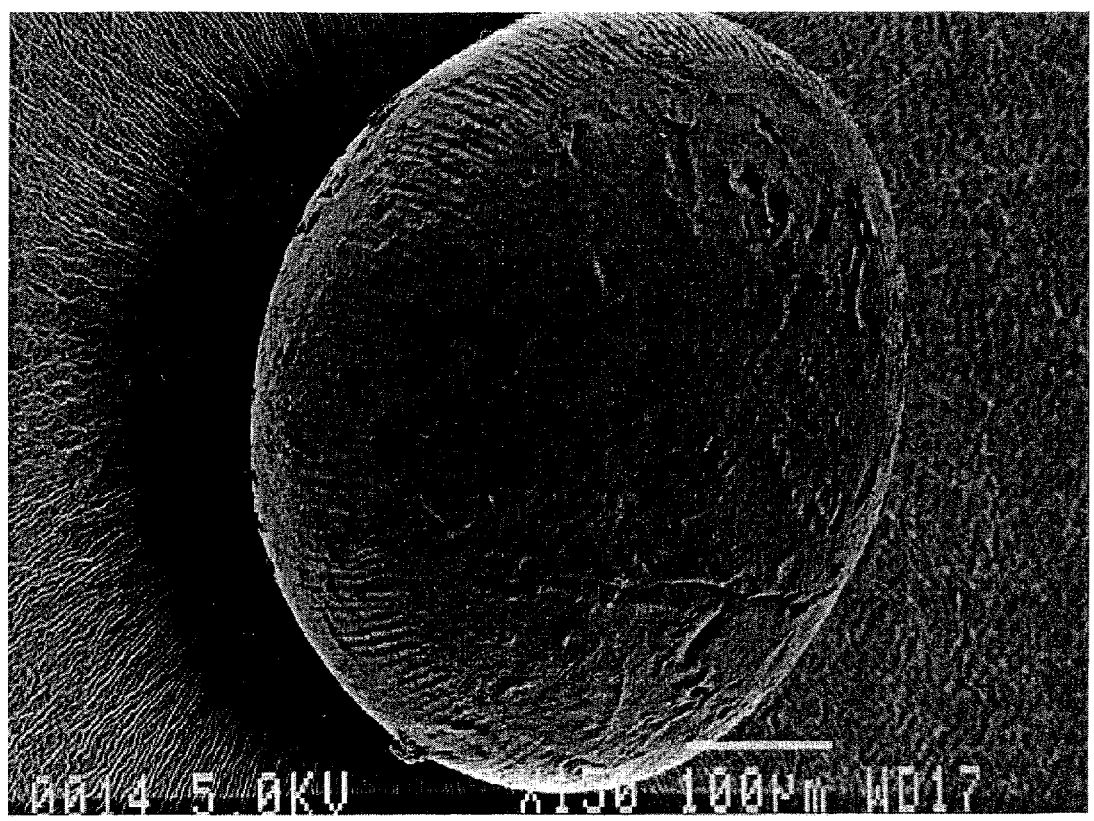
FIG. 2B is a scanning electron microscope (SEM) photograph of the embolic particle surface and FIGS. 2C–2E are cross-sections of embolic particles.
Figure 2C:
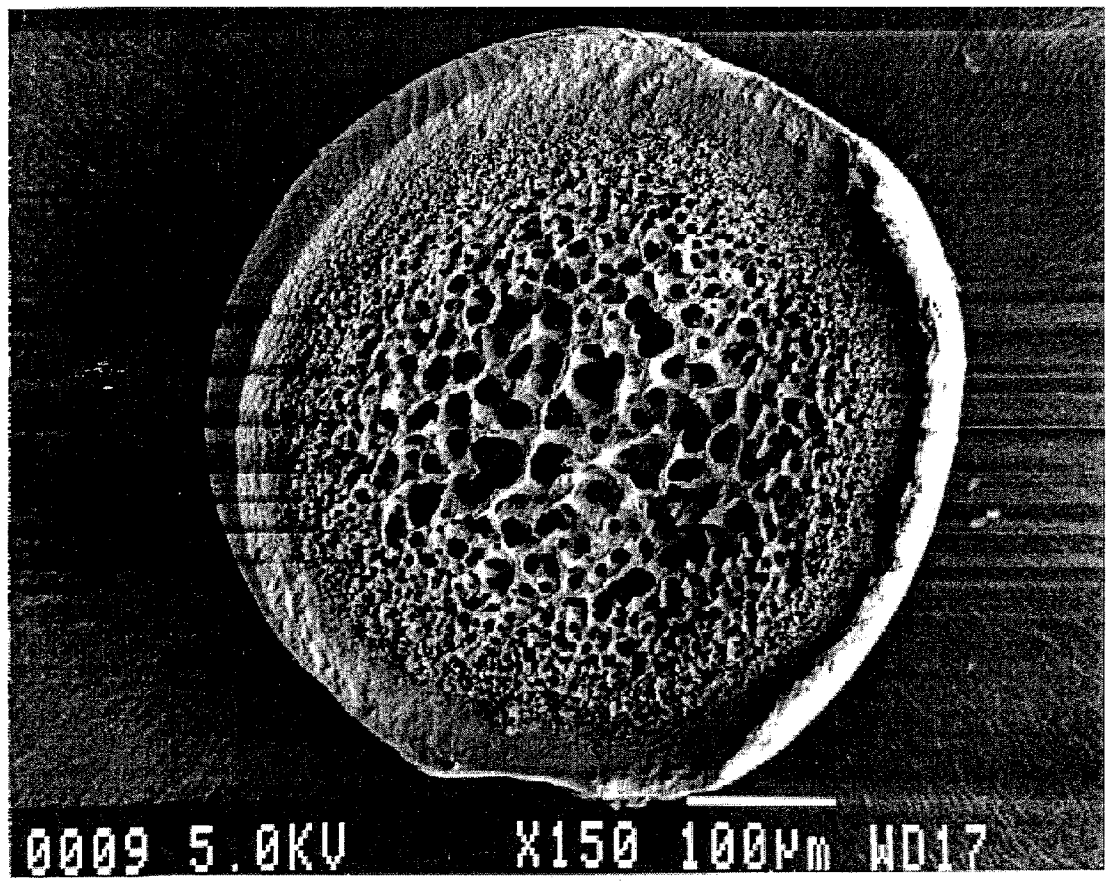
Figure 2D:
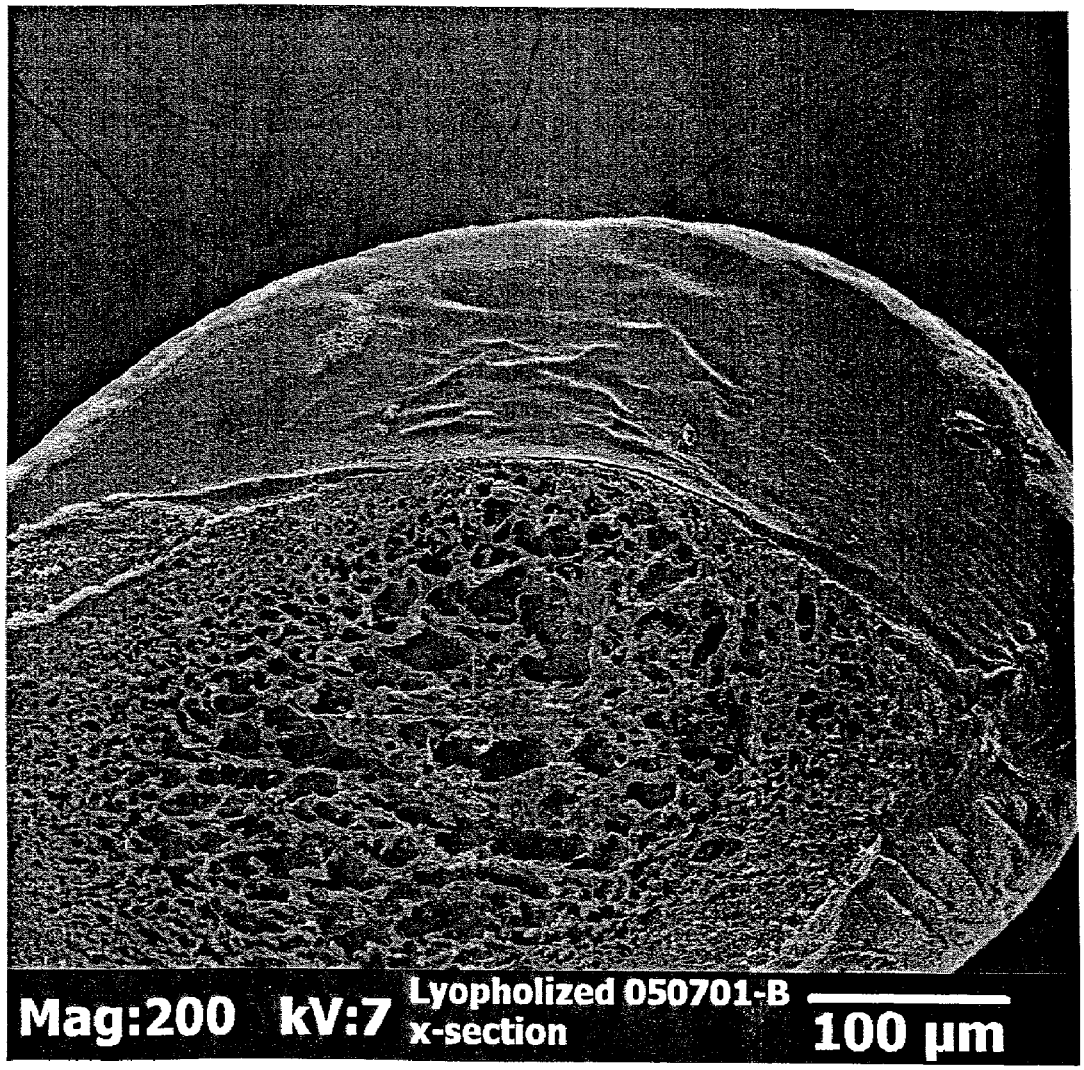
Figure 2E:
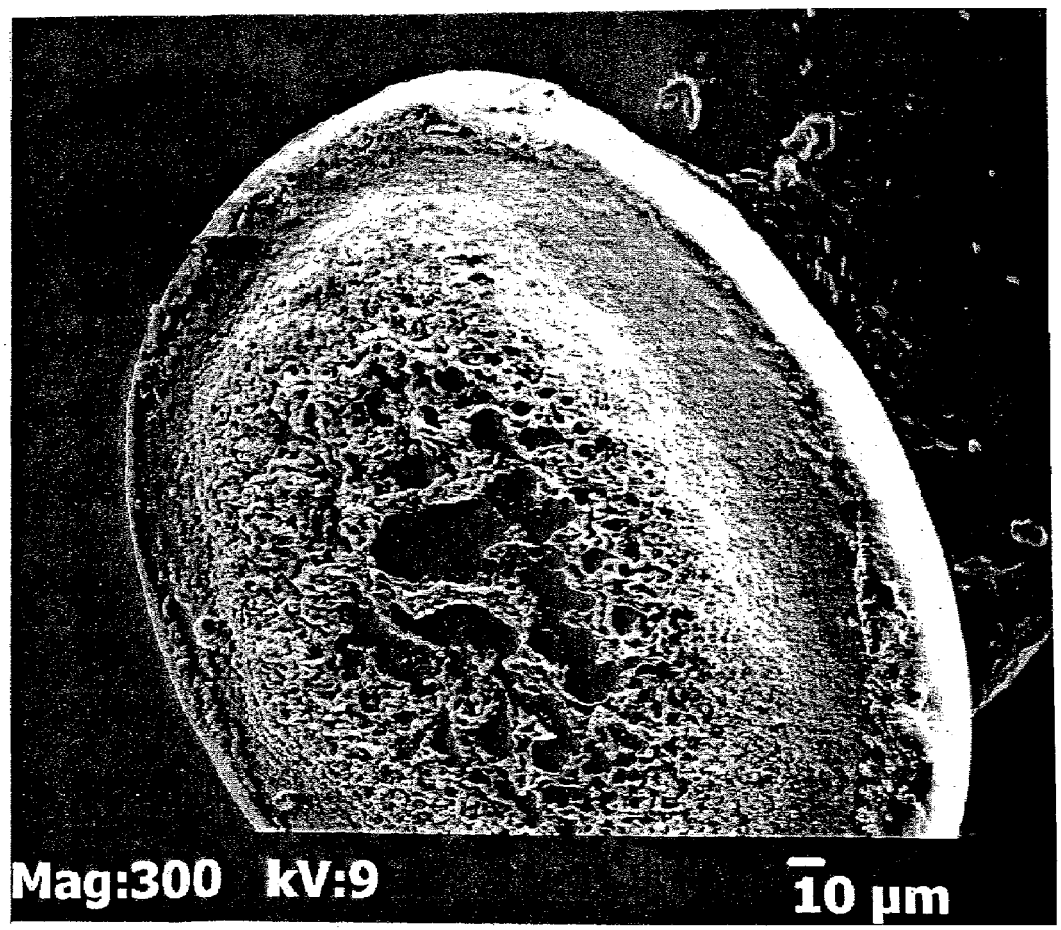

Referring to FIG. 2A, embolic particles 111 have a substantially uniform spherical shape and size. Referring to FIG. 2B, each embolic particle has a well-defined outer spherical surface including relatively small, randomly located pores. The surface appears substantially smooth, with some larger surface morphology such as crevice-like features. Referring to FIGS. 2C–2E, SEM images of cross-sections through embolic particles, the body of the particle defines pores which provide compressibility and other properties to the embolic composition. Pores near the center of the particle are relatively large and pores near the surface of the particle are relatively small.

The region of small pores near the periphery of the embolic particle is relatively stiff and incompressible, which enhances resistance to shear forces and abrasion. In addition, the variable pore size profile produces a symmetric compressibility and, it is believed, a compressibility profile such that the particles are relatively easily compressed from a maximum, at rest diameter to a smaller, compressed first diameter but compression to even smaller diameter requires substantially greater force. A variable compressibility profile is believed to be due to the presence of a relative weak, collapsible inter-pore wall structure in the center region where the pores are large, and a stiffer inter-pore wall structure near the surface of the particle, where the pores are more numerous and relatively small. The variable pore size profile also is believed to enhance elastic recovery after compression. The pore structure also influences the density of the embolic particles and the rate of carrier fluid or body fluid uptake.

The embolic particles can be delivered through a catheter having a lumen area that is smaller, e.g. 50% smaller or less, than the uncompressed cross-sectional area of the particles. As a result, the embolic particles must be compressed to pass through the catheter for delivery into the body. The compression force is provided indirectly by increasing the pressure applied to the carrier fluid by depressing the syringe plunger. The embolic particles are relatively easily compressed to diameters sufficient for delivery through the catheter into the body. The robust, rigid surface region resists abrasion when the embolic particles contact hard surfaces such as syringe surfaces, hard plastic or metal stopcock surfaces, and the catheter lumen wall (e.g. Teflon) during delivery. Once in the body, the embolic particles substantially recover to original diameter and shape for efficient transport in the carrier and body fluid stream. At the point of occlusion, the particles can again compress as they aggregate in the occlusion region. The embolic particles form a dense occluding mass. The compression in the body is determined by the force provided by body fluid flow in the lumen. The compression may be limited by the compression profile of the particles and the number of embolic particles needed to occlude a given diameter may be reduced.

In embodiments, the particles have a diameter of about 1500 or 1200 microns or less, and about 10 microns or more, e.g. about 400 microns or more and the pores are about 50 or 35 to 0.01 micron. The embolic particles can be classified in size ranges of about 500–700 microns, about 700–900 microns, or about 900–1200 microns. The particles typically have a mean diameter in approximately the middle of the range and variance of about 20% or less, e.g. 15% or 10% or less.

Referring particularly to FIG. 2C, the particles can be considered to include a center region, C, from the center of the particle to a radius of about r/3, a body region, B, from about r/3 to about 2 r/3 and a surface region, S, from 2r/3 to r. The regions can be characterized by the relative size of the pores and the number of pores of given sizes. In embodiments, the center region has a greater number of relatively large pores than the body region and the surface region. The large pores are in the range of about 20 micron or more, e.g. 30 micron or more, or in the range of about 20 to 35 micron. The body region has a greater number of intermediate size pores than the surface region. The intermediate size pores are in the range of about 5 to 18 micron. In embodiments, the regions may also have different densities, with the density of the surface region being greater than the density of the body region, and the density of the body region being greater than the density of the center region.

The size of the pores in each of the regions can also be characterized by a distribution. In embodiments, the predominant pore size(s) in the center region being greater than the predominant pore size(s) in the body region and the predominant pore size(s) in the body region is greater than the predominant pore size(s) in the surface region. In embodiments, in the predominant pore size in the center region is 20 micron or more, e.g. 30 microns or more, or in the range of about 20 to 35 microns. The predominant pore size in the body region is about 18 micron or less, e.g. about 15 micron or less, or in the range of about 18 to 2 micron. The pores in the surface region are preferably predominantly less than about 1 micron, e.g. about 0.1 to 0.01 micron.

In embodiments, the predominant pore size in the body region is about 50 to 70% of the pore size in the center region and the pore size in the surface region is about 10% or less, e.g. about 2% of the pore size in the body region. The size of the pores on the outer surface of the particle is predominantly in the range of about 1 micron or less, e.g. about 0.1 or 0.01 micron. In embodiments, the surface and/or surface region is substantially free of pores having a diameter larger than about 10 micron or larger than about 1 micron. In embodiments, the predominant pore size is in the region 0.8 or 0.9r to r is about 1 micron or less, e.g. 0.5 to 0.1 micron or less. The region from the center of the particle to 0.8 or 0.9r has pores of about 10 micron or greater and/or has a predominant pore size of about 2 to 35 micron. In embodiments, the predominant pore size in the region 0.8 or 0.9r to r is about 5% or less, e.g. 1% or 0.3% or less than the predominant pore size in the region from the center to 0.9r. the largest pores in the particles can have a size in the range of 1% or 5% or 10% or more of the particle diameter.

The size of the pores can be measured by viewing a cross-section as in FIG. 2C. For irregularly shaped pores, the maximum visible cross-section is used. The predominant pore size(s) can be found by measuring the size of the visible pores and plotting the number of pores as a function of size. The predominant pore size(s) are the sizes that are about the maximum in the distribution. In FIG. 2C, the SEM was taken on wet particles including absorbed saline, which were frozen in liquid nitrogen and sectioned. (FIG. 2B was taken prior to sectioning.) In FIGS. 2D and 2E, the particle was freeze-dried prior to sectioning and SEM analysis.

The density of the particles is such that they are readily suspended in the carrier fluid such as a mixture of saline and contrast solution and remain suspended during delivery. In embodiments, the density is in about 1.1–1.4 g/cm$^3$. For suspension in a saline-contrast solution, the density is about 1.2–1.3 g/cm$^3$. The sphericity after compression in a catheter to about 50% or more of their cross-sectional area is about 0.90 or 0.95 or greater. In embodiments, the particles can be manually compressed, essentially flattened, while wet to less than 50% of original diameter and then, upon exposure to fluid, regain a sphericity of about 0.9 or more. The carrier fluid is a pharmaceutically acceptable carrier such as saline or contrast agent. The particles can be sterilized prior to use.

Manufacture

Figure 3A:
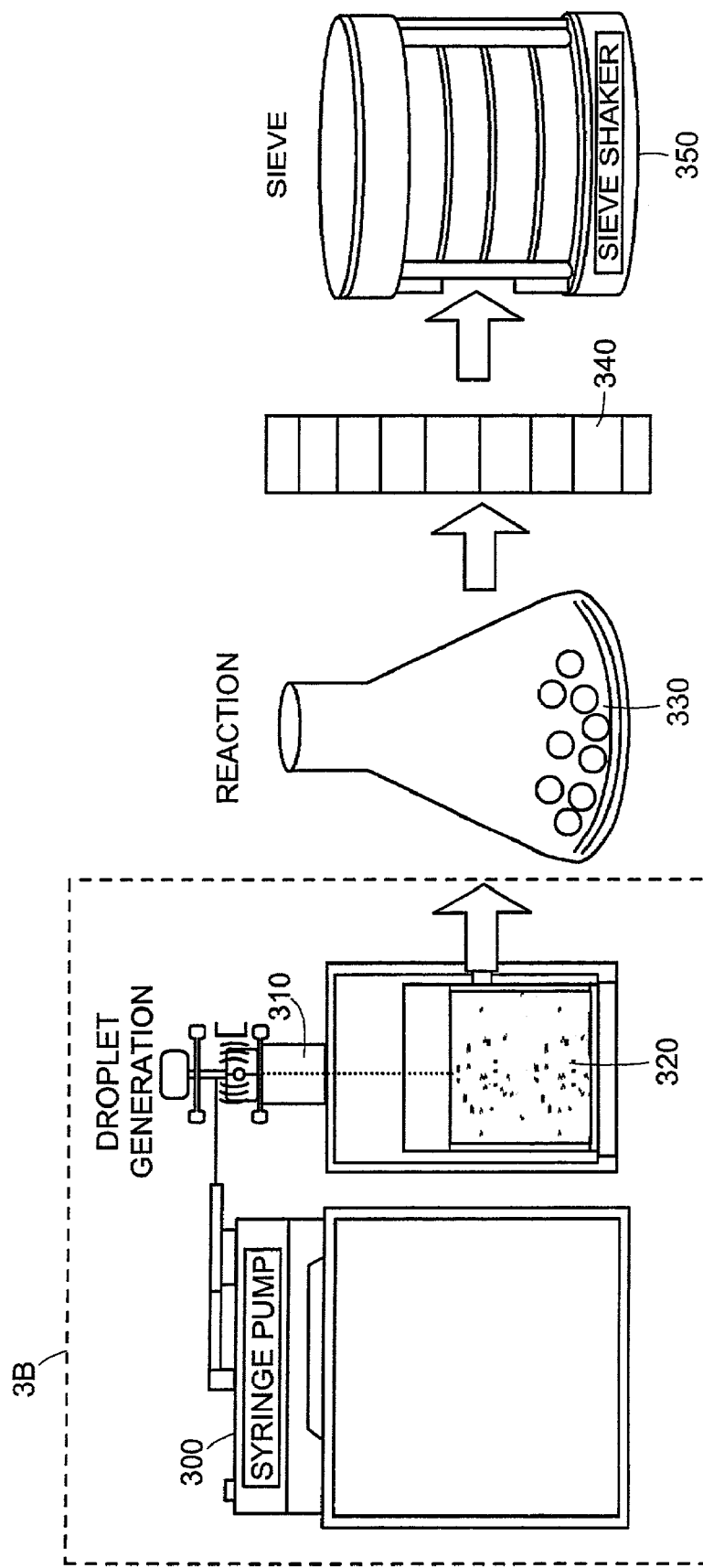

Referring to FIG. 3A, a system for producing embolic particles includes a flow controller 300, a drop generator 310, a gelling vessel 320, a reactor vessel 330, a gel dissolution chamber 340 and a filter 350. The flow controller 300 delivers polymer solutions to a viscosity controller 305, which heats the solution to reduce viscosity prior to delivery to the drop generator 310. The drop generator 310 forms and directs drops into a gelling vessel 320, where drops are stabilized by gel formation. The gel-stabilized drops are transferred from the gelling vessel 320 to reactor vessel 330 where the polymer in the gel-stabilized drops are reacted forming precursor particles. The precursor particles are transferred to a gel dissolution chamber 340, where the gel is dissolved. The particles are then filtered in a filter 350 to remove debris, sterilized, and packaged as an embolic composition including embolic particles.

A base polymer and a gelling precursor are dissolved in water and mixed. The mixture is introduced to a high pressure pumping apparatus, such as a syringe pump (e.g., model PHD4400, Harvard Apparatus, Holliston, Mass.). Examples of base polymers include polyvinyl alcohol, polyacrylic acid, polymethacrylic acid, poly vinyl sulfonate, carboxymethyl cellulose, hydroxyethyl cellulose, substituted cellulose, polyacrylamide, polyethylene glycol, polyamides, polyureas, polyurethanes, polyester, polyethers, polystyrene, polysaccharide, polylactic acid, polyethylene, polymethylmethacrylate and copolymers or mixtures thereof. A preferred polymer is polyvinyl alcohol. The polyvinyl alcohol, in particular, is hydrolyzed in the range of 80 to 99%. The weight average molecular weight of the base polymer can be in the range of 9000 to 186,000, 85,000 to 146,000 or 89,000 to 98,000. Gelling precursors include, for example, alginates, alginate salts, xanthan gums, natural gum, agar, agarose, chitosan, carrageenan, fucoidan, furcellaran, laminaran, hypnea, eucheuma, gum arabic, gum ghatti, gum karaya, gum tragacanth, hyalauronic acid, locust beam gum, arabinogalactan, pectin, amylopectin, other water soluble polysaccharides and other ionically crosslinkable polymers. A particular gelling precursor is sodium alginate. A preferred sodium alginate is high guluronic acid, stem-derived alginate (e.g. about 50 or 60% or more guluronic acid with a low viscosity e.g. about 20 to 80 cps at 20° C.) which produces a high tensile, robust gel. High molecular weight PVA is dissolved in water by heating, typically above about 70° C., while alginates can be dissolved at room temperature. The PVA can be dissolved by mixing PVA and alginate together in a vessel which is heated to autoclave temperature (about 121° C.). Alternatively, the PVA can be disposed in water and heated and the alginate subsequently added at room temperature to avoid exposing the alginate to high temperature. Heat can also be applied by microwave application. In embodiments, for PVA/alginate, the mixture is typically about 7.5 to 8.5%, e.g. about 8% by weight PVA and about 1.5 to 2.5%, e.g. about 2%, by weight alginate.

Figure 3B:
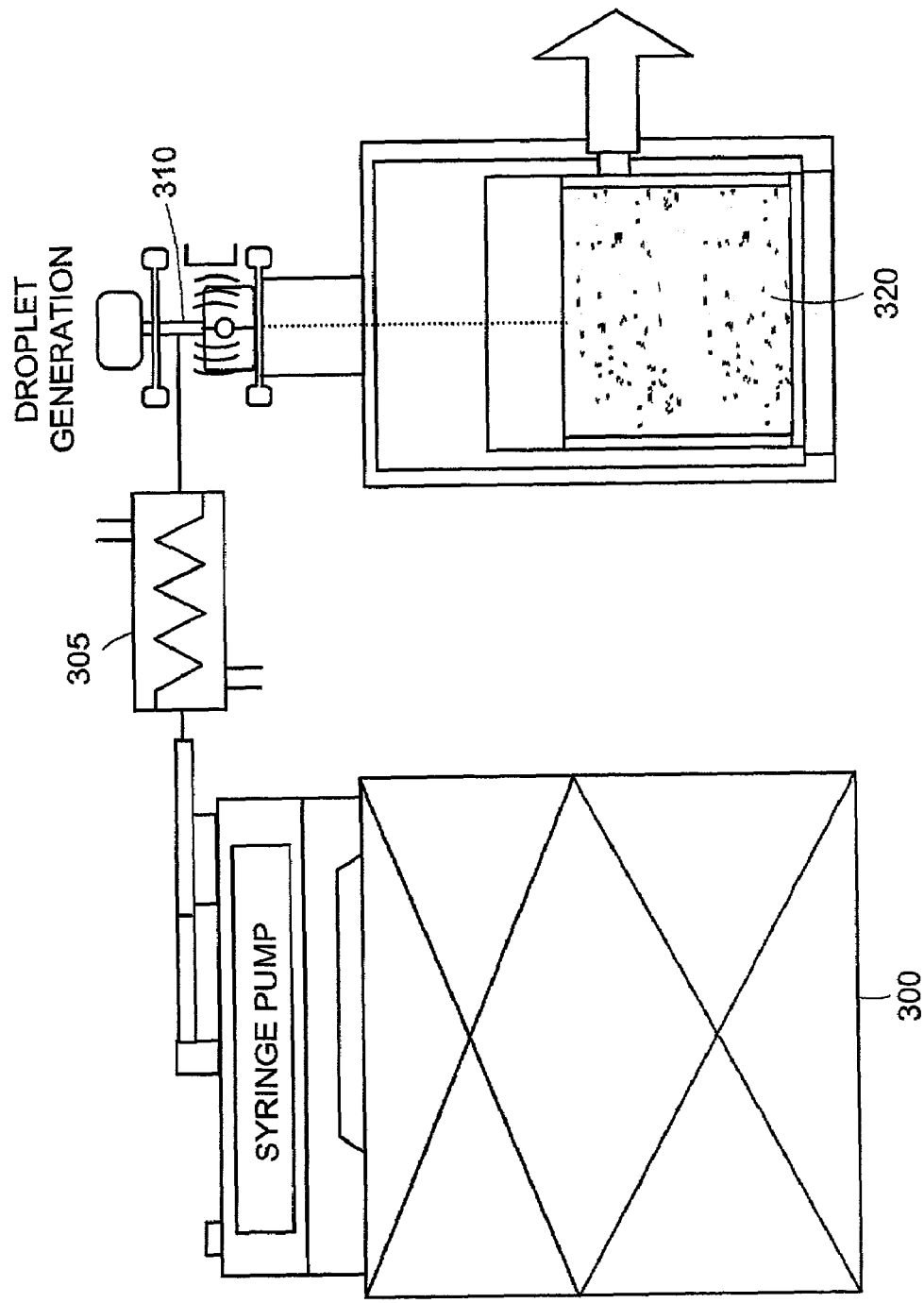
FIG. 3B is an enlarged schematic of region A in FIG. 3A.

Referring to FIG. 3B, the viscosity controller 305 is a heat exchanger circulating water at a predetermined temperature about the flow tubing between the pump and drop generator. The mixture of base polymer and gelling precursor flows into the viscosity controller 305, where the mixture is heated so that its viscosity is lowered to a level for efficient formation of very small drops. For a high molecular weight PVA/alginate solution, the temperature of the circulating water is less than about 75° C. and more than about 60° C., for example, 65° C. which maintains the mixture at a viscosity of 90–200 centipoise. For spherical particles, the viscosity of the drops is maintained so they are captured in the gelling vessel without splintering or cojoining which can create irregular, fiberous particles. In other embodiments, the flow controller and/or the drop generator can be placed in a temperature-controlled chamber, e.g. an oven, or a heat tape wrap, to maintain a desired viscosity.

The drop generator 310 generates substantially spherical drops of predetermined diameter by forcing a stream of the mixture of base polymer and gelling precursor through a nozzle which is subject to a periodic disturbance to break up the jet stream into drops. The jet stream can be broken into drops by vibratory action generated for example, by an electrostatic or piezoelectric element. The drop size is controlled by controlling the flow rate, viscosity, amplitude, and frequency at which the element is driven. Lower flow rates and higher frequencies produce smaller drops. A suitable electrostatic drop generator is available from NISCO Engineering, model NISCO Encapsulation unit VAR D, Zurich, Switzerland. In embodiments, the frequency is in the range of about 0.1 to 0.8 kHz. The flow rate through the droplet generator is in the range of about 1 to 12 mL per minute. The drop generator can include charging the drops after formation such that mutual repulsion between drops prevents drop aggregation as drops travel from the generator to the gelling vessels. Charging may be achieved by, e.g. an electrostatic charging device such as a charged ring positioned downstream of the nozzle.

Drops of the base polymer and gelling precursor mixture are captured in the gelling vessel 320. The gelling vessel 320 contains a gelling agent which interacts with the gelling precursor to stabilize drops by forming a stable gel. Suitable gelling agents include, for example, a divalent cation such as alkali metal salt, alkaline earth metal salt or a transition metal salt that can ionically crosslink with the gelling agent. An inorganic salt, for example, a calcium, barium, zinc or magnesium salt can be used as a gelling agent. In embodiments, particularly those using an alginate gelling precursor, a suitable gelling agent is calcium chloride. The calcium cations have an affinity for carboxylic groups in the gelling precursor. The cations complex with carboxylic groups in the gelling precursor resulting in encapsulation of the base polymer in a matrix of gelling precursor.

Figure 4:
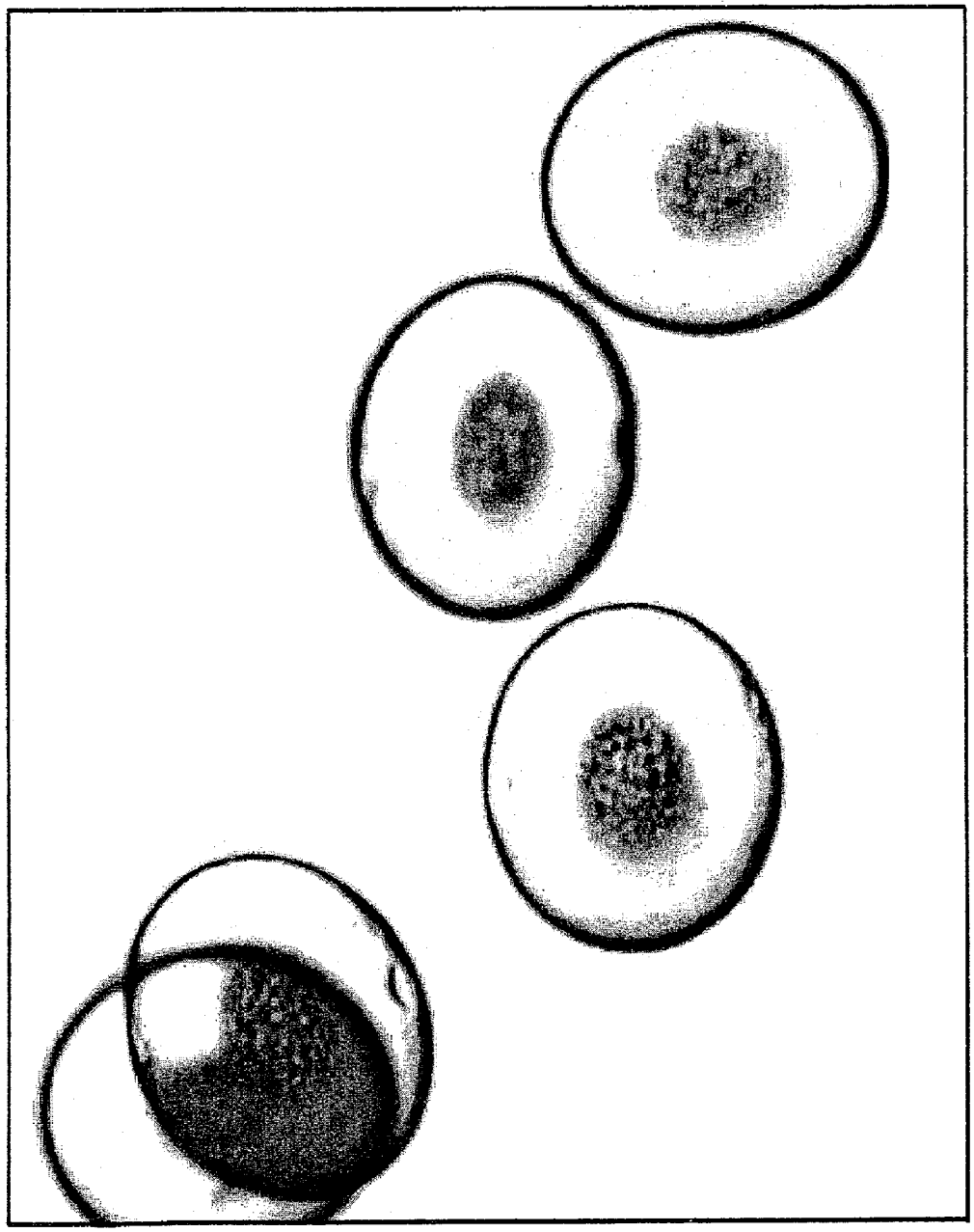
FIG. 4 is a photograph of gel-stabilized drops.

Referring to FIG. 4, a photo-image of the gelled particles, the gelling agent is in an amount selected in accordance with the desired properties of the particles. As evident, a pore structure in the particle forms in the gelling stage. The concentration of the gelling agent can control pore formation in the particle, thereby controlling the porosity gradient in the embolic particle. Adding non-gelling ions, for example, sodium ions, to the gelling solution can reduce the porosity gradient, resulting in a more uniform intermediate porosity throughout the particle. In embodiments, the gelling agent is, for example, 0.01–10 weight percent, 1–5 weight percent or 2 weight percent in deionized water. In embodiments, particles, including gelling agent and a pore structure can be used in embolic compositions.

Following drop stabilization, the gelling solution is decanted from the solid drops and the stabilized drops are transferred to the reactor vessel 330. In the reactor vessel 330, the stabilized drops are reacted to produce precursor particles. The reactor vessel includes an agent that chemically reacts with the base polymer, e.g. to cause crosslinking between polymer chains and/or within a polymer chain. The agent diffuses into the stabilized drops from the surface of the particle in a gradient which, it is believed, provides more crosslinking near the surface of the stabilized drop compared to the body and center of the drop. Reaction is greatest at the surface of the drop, providing a stiff, abrasion resistant exterior. For polyvinyl alcohol, for example, the vessel 330 includes aldehydes, such as formaldehyde, glyoxal, benzaldehyde, aterephthalaldehyde, succinaldehyde and glutaraldehyde for the acetalization of polyvinyl alcohol. The vessel 330 also includes an acid, for example, strong acids such as sulfuric acid, hydrochloric acid, nitric acid and weak acids such as acetic acid, formic acid and phosphoric acid. In embodiments, the reaction is primarily a 1,3 acetalization:

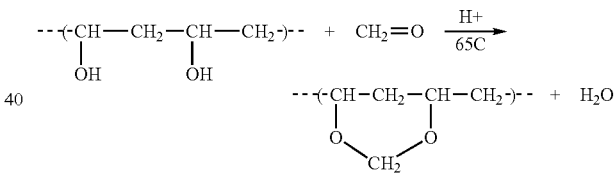

This intra-chain acetalization reaction can be carried out with relatively low probability of inter-chain crosslinking as described in John G. Pritchard "Poly(Vinyl Alcohol) Basic Properties And Uses (Polymer Monograph, vol. 4) (see p. 93–97), Gordon and Breach, Science Publishers LTD., London, 1970, the entire contents of which is hereby incorporated by reference. Some OH groups along a polymer chain may remain unconverted since the reaction proceeds in a random fashion and there will be left over OH groups that do not react with adjacent groups.

Adjusting the amount of aldehyde and acid used, reaction time and reaction temperature can control the degree of acetalization. In embodiments, the reaction time is e.g., 5 minutes to 1 hour, 10 to 40 minutes or 20 minutes. The reaction temperature can be 25° C. to 150° C. or 75° C. to 130° C. or 65° C. The reactor vessel is placed in a water bath fitted with a orbital motion mixer. The crosslinked precursor particles are washed several times with deionized water to neutralize the particles and remove any residual acidic solution.

The precursor particles are transferred to the dissolution chamber 340 to remove the gelling precursor, e.g. by an ion exchange reaction. In embodiments, sodium alginate is removed by ion exchange with a solution of sodium hexa-metaphosphate (EM Science). The solution can include, for example, ethylenediaminetetracetic acid (EDTA), citric acid, other acids and phosphates. The concentration of the sodium hexa-metaphosphate can be, for example, 1–20 weight %, 1–10 weight % or 5 weight % in deionized water. Residual gelling precursor, for example, sodium alginate, can be determined by assay for detection of uronic acids in, for example, alginates containing mannuronic and guluronic acid residues. Suitable assays include rinsing the particles with sodium tetraborate in sulfuric acid solution to extract alginate and combining the extract with metahydroxydiphenyl colormetric reagent and determining concentration by UV/VIS spectroscopy. Testing can be carried out by alginate suppliers such as FMC Biopolymer, Oslo, Norway. Residual alginate may be present in the range of about 20–35% by weight prior to rinsing and in the range of about 0.01–0.5% or 0.1–0.3% or 0.18% in the particles after rinsing for 30 minutes in water at about 23° C.

The particles are filtered through filter 350 to remove residual debris. Particles of 500 to 700 microns are filtered through a sieve of 710 microns and then a sieve of 300 microns. Particles of 700 to 900 microns are filtered through a sieve of 1000 microns and then a sieve of 500 microns. Particles of 900 to 1200 microns are filtered through a sieve of 1180 microns and then a sieve of 710 microns.

The filtered particles are sterilized by a low temperature technique such as e-beam irradiation, and packaged, typically about 1 to 5 ml of particles in about 5 to 10 ml saline. In embodiments, electron beam irradiation can be used to pharmaceutically sterilize the particles to reduce bioburden. In e-beam sterilization, an electron beam is accelerated using magnetic and electric fields, and focused into a beam of energy. This resultant beam can be scanned by means of an electromagnet to produce a "curtain" of accelerated electrons. The accelerated electron beam penetrates the collection of embolic particles to confer upon them electrons which destroy bacteria and mold to sterilize and reduce the bioburden in the embolic particles. Electron beam sterilization can be carried out by sterilization vendors such as Titan Scan, Lima, Ohio.

EXAMPLES

Example 1

Embolic particles are manufactured from an aqueous solution containing 8 weight % of polyvinyl alcohol, 99+% hydrolyzed, average $M_w$ 89,000–120,000 (ALDRICH) and 2 weight % of gelling precursor, sodium alginate, PRONOVA UPLVG, (FMC BioPolymer, Princeton, N.J.) in deionized water and the mixture is heated to about 121° C. The solution has a viscosity of about 310 centipoise at room temperature and a viscosity of about 160 cps at 65° C. Using a syringe pump (Harvard Apparatus), the mixture is fed to drop generator (Nisco Engineering). Drops are directed into a gelling vessel containing 2 weight % of calcium chloride in deionized water and stirred with a stirring bar. The calcium chloride solution is decanted within about three minutes to avoid substantial leaching of the polyvinyl alcohol from the drops into the solution. The drops are added to the reaction vessel containing a solution of 4% by weight of formaldehyde (37 wt % in methanol) and 20% by weight sulfuric acid (95–98% concentrated). The reaction solution is stirred at 65° C. for 20 minutes. Precursor particles are rinsed with deionized water (3×300 mL) to remove residual acidic solution. The sodium alginate is substantially removed by soaking the precursor particles in a solution of 5 weight % of sodium hexa-methaphosphate in deionized water for 0.5 hour. The solution is rinsed in deionized water to remove residual phosphate and alginate. The particles are filtered by sieving, as discussed above, placed in saline (USP 0.9% NaCl) and followed by irradiation sterilization.

Particles were produced at the nozzle diameters, nozzle frequencies and flow rates (amplitude about 80% of maximum) described in Table I.

TABLE 1

| Bead Size (microns) | Nozzle Diameter (microns) | Frequency (kHz) | Flow Rate (mL/min) | Density (g/mL) | Sphericity | Suspendability (minutes) |
|---|---|---|---|---|---|---|
| 500–700 | 150 | 0.45 | 4 | — | 0.92 | 3 |
| 700–900 | 200 | 0.21 | 5 | 1.265 | 0.94 | 5 |
| 900–1200 | 300 | 0.22 | 10 | — | 0.95 | 6 |

Suspendability is measured at room temperature by mixing a solution of 2 ml of particles in 5 ml saline with contrast solution (Omnipaque 300, Nycomed, Buckinghamshire, UK) and observing the time for about 50% of the particles to enter suspension, i.e. have not sunk to the bottom or floated to the top of a container (about 10 ml, 25 mm dia vial). Suspendability provides a practical measure of how long the particles will remain suspended in use. (Omnipaque is an aqueous solution of Iohexol, N.N.-Bis (2,3-dihydroxypropyl)-T-[N-(2,3-dihydroxypropyl)-acetamide]-2,4,6-trilodo-isophthalamide; Omnipaque 300 contains 647 mg of iohexol equivalent to 300 mg of organic iodine per ml. The specific gravity of 1.349 of 37° C. and an absolute viscosity 11.8 cp at 20° C.) The particles remain in suspension for about 2 to 3 minutes.

Particle size uniformity and sphericity is measured using a Beckman Coulter RapidVUE Image Analyzer version 2.06 (Beckman Coulter, Miami, Fla.). Briefly, the RapidVUE takes an image of continuous-tone (gray-scale) form and converts it to a digital form through the process of sampling and quantization. The system software identifies and measures particles in an image in the form of a fiber, rod or sphere. Sphericity computation and other statistical definitions are in Appendix A, attached, which is a page from the RapidVUE operating manual.

Figure 5:
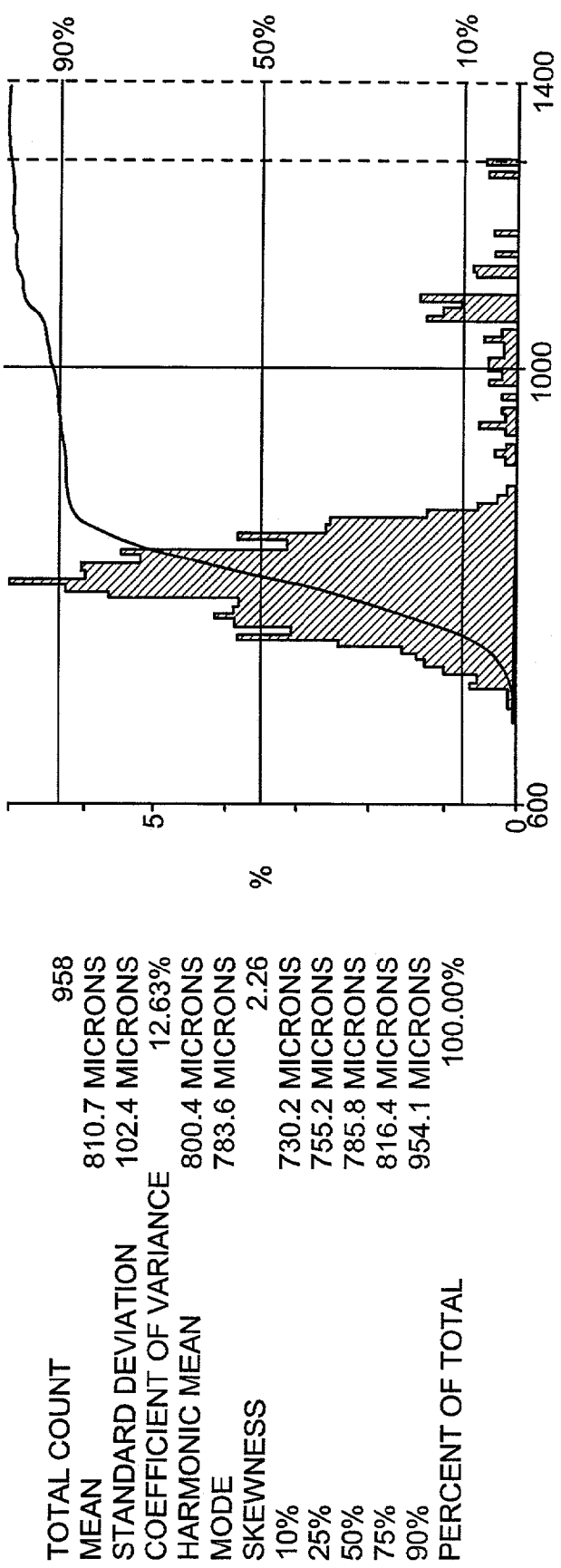
FIG. 5 is a graph of embolic particle size uniformity.

Referring to FIG. 5, particle size uniformity is illustrated for particles 700–900 micron. The x-axis is the particle diameter. The y-axis is the volume normalized percentage of particles at each particle size. The total volume of particles detected is computed and the volume of the particles at each diameter is divided by the total volume. The embolic particles have distribution of particle sizes with variance of less than about ±15%.

Example 2

Figure 6:
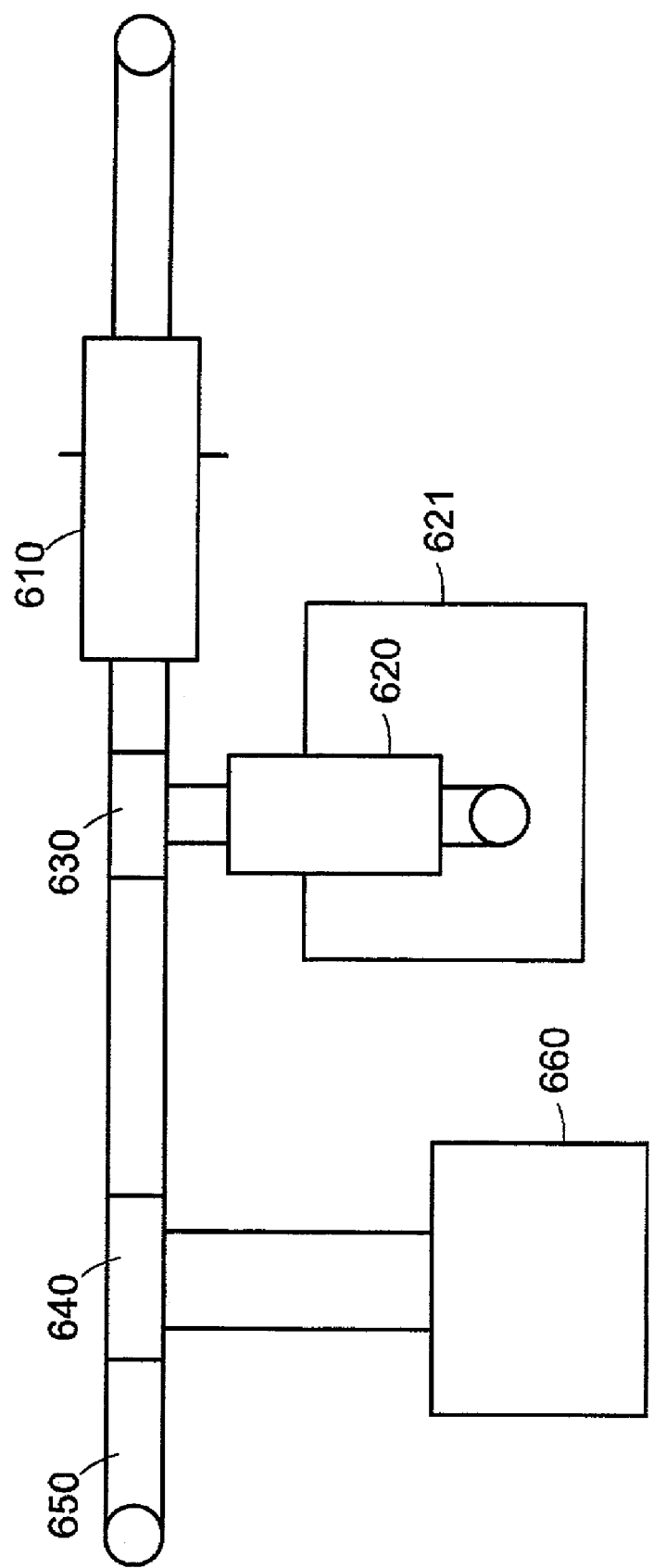
FIG. 6 is a schematic of an injection pressure testing equipment.

Referring to FIG. 6, a catheter compression test investigates the injectability, and indirectly, the compressibility of the particles. The test apparatus includes a reservoir syringe 610 and an injection syringe 620 coupled to a T-valve 630. Syringe 610 is a 20 mL syringe while injection syringe 620 is a 3 mL syringe. T-valve 630 is coupled in series to a second T-valve 640. T-valve 640 is coupled to a catheter 650 and a pressure transducer 660. Injection syringe 620 is coupled to a syringe pump 621 (Harvard Apparatus).

To test deliverability of the particles, syringe 610 and syringe 620 are loaded with embolic composition in saline and contrast (50/50 Ominipaque 300). The embolic composition in syringes 610 and 620 is intermixed by turning the T-valve to allow fluid between the syringes to mix and suspend the particles. After mixing, the embolic composition in syringe 620 flows at a rate of about 10 mL/min. The back pressure generated in the catheter 650 is measured by the pressure transducer 670 in millivolts to measure the clogging of catheter 650. About 1 ml of the particles is mixed in 10 mL of solution.

Results for several different catheters (available from Boston Scientific, Natick, Mass.) and particle sizes are shown in Table 2. The baseline pressure is the pressure observed when injecting carrier fluid only. The delivery pressure is the pressure observed while delivering particles in carrier fluid. The average is the average of the peak pressure observed in the three runs.

| SIZE (microns) | Delivery Catheter | Inner Diameter (inches) | Avg. Baseline Pressure (psia) | Avg. Delivery Pressure (psia) | Total number of Clogs |
|---|---|---|---|---|---|
| 500–700 | RENEGADE ® | 0.021 (533 micron) | 32.610 | 33.245 | 0 |
| 700–900 | FASTRACKER ® | 0.024 (609 micron) | 11.869 | 13.735 | 0 |
| 900–1200 | GLIDECATH ® | 0.038 (965 micron) | 0.788 | 0.864 | 0 |

As evident, particles in each of the size ranges were successfully delivered without clogging through catheters having a lumen diameter smaller than the largest particle size. The particles exhibit a post-compression sphericity of about 0.9 or more.

Example 4

Solubility is tested by mixing particles in a solution of solvent at room temperature for about 0.5 hour and observing the mixture for visible signs of dissolution. The particles are insoluble in DMSO (Dimethylsulfoxide), HFIP (Hexafluoroisopropanol), and THF (Tetrahydrafuran).

Example 5

Embolic particles include the following glass transition temperatures as measured by differential scanning calorimetry data (DSC)

| Product | 500–700 microns | 900–1200 microns |
|---|---|---|
| Glass transition temperature (Tg) | 109.30–110.14 | 108.30–111.87 |

Example 6

Figure 7:
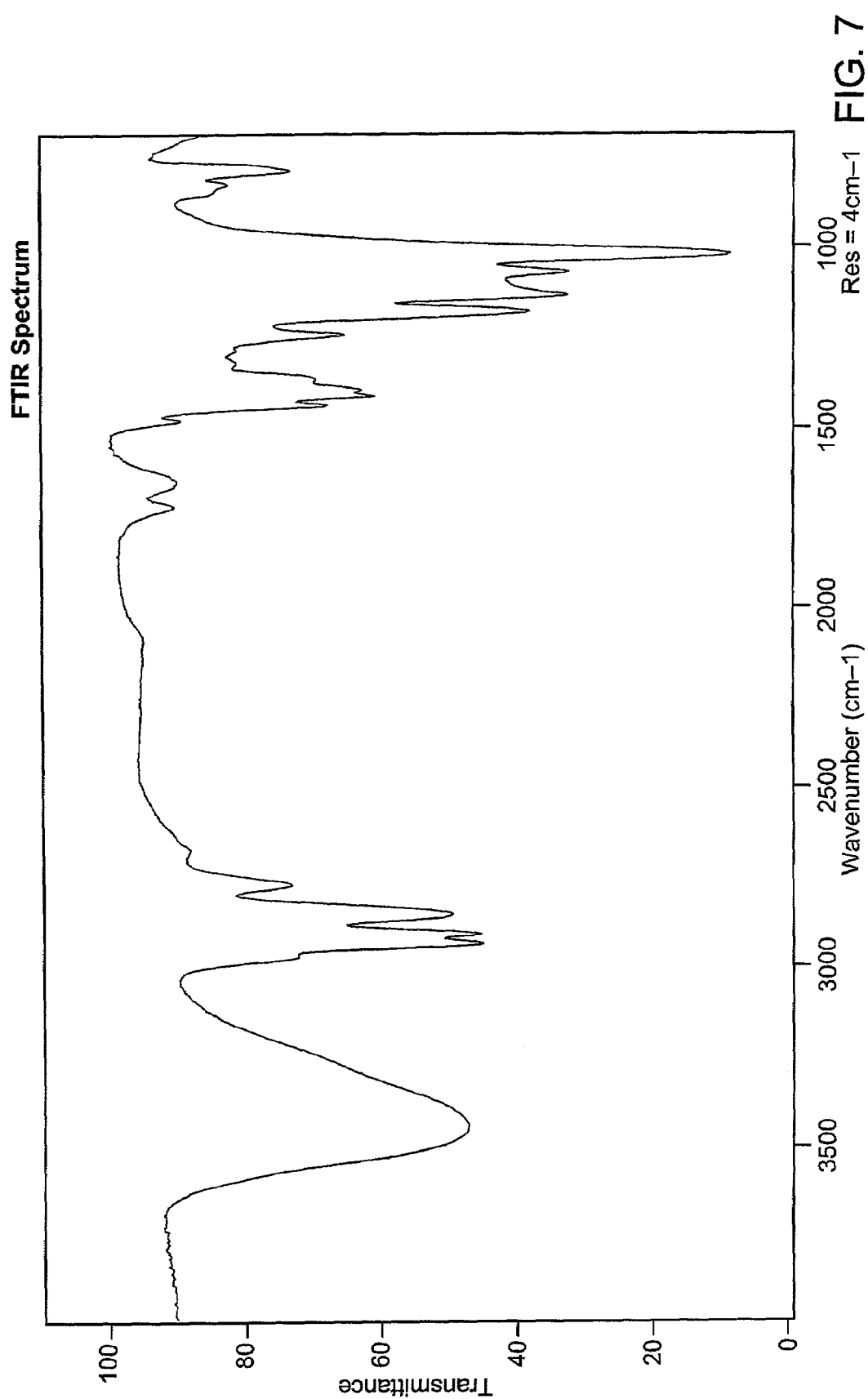
FIG. 7 is an infrared spectrum of embolic particles.

Referring to FIG. 7, an ATR infrared spectrum of dried particles is provided.

Use

The embolic compositions can be used as pharmaceutically acceptable compositions in the treatment of, for example, fibroids, tumors, internal bleeding, AVMs, hypervascular tumors, fillers for aneurysm sacs, endoleak sealants, arterial sealants, puncture sealants and occlusion of other lumens such as fallopian tubes. Fibroids can include uterine fibroids which grow within the uterine wall (intramural type), on the outside of the uterus (subserosal type), inside the uterine cavity (submucosal type), between the layers of broad ligament supporting the uterus (interligamentous type), attached to another organ (parasitic type), or on a mushroom-like stalk (pedunculated type). Internal bleeding includes gastrointestinal, urinary, renal and varicose bleeding. AVMs are for example, abnormal collections of blood vessels, e.g. in the brain, which shunt blood from a high pressure artery to a low pressure vein, resulting in hypoxia and malnutrition of those regions from which the blood is diverted.

The magnitude of a therapeutic dose of the embolic composition can vary based on the nature, location and severity of the condition to be treated and the route of administration. A physician treating the condition, disease or disorder can determine effective amount of embolic composition. An effective amount of embolic composition refers to the amount sufficient to result in amelioration of symptoms or a prolongation of survival of the patient. The embolic compositions can be administered as pharmaceutically acceptable compositions to a patient in any therapeutically acceptable dosage, including those administered to a patient intravenously, subcutaneously, percutaneously, intratrachealy, intramuscularly, intramucosaly, intracutaneously, intra-articularly, orally or parenterally.

Compositions containing the embolic particles can be prepared in calibrated concentrations of the embolic particles for ease of delivery by the physician. The density of the composition can be from about 1.1 to 1.4 g/cm$^3$, or from about 1.2 to about 1.3 g/cm$^3$ in saline solution. Suspensions of the embolic particles in saline solution can be prepared to form stable suspensions over duration of time. The suspensions of embolic particles can be stable from 1 to 10 minutes, 2–7 minutes or 3 to 6 minutes. The physician can determine concentration of embolic particles by adjusting the weight ratio of the embolic particles to physiological solution. If weight ratio of the embolic particles is too small, too much liquid could be injected in a blood vessel, possibly allowing the embolic particles to stray into lateral vessels. In embodiments, the weight ratio of the embolic particles to the physiological solution is about 0.01 to 15% by weight. The embolic composition can include a mixture of particles including particles with the pore profiles discussed above and particles with other pore profiles or non-porous particles. Particles can be used for embolic applications without removal of the gelling agent (e.g. alginate) for example at the stabilized drop stage or precursor particle stages described above. While substantially spherical particles are preferred, non-spherical particles can be manufactured and formed by controlling, e.g. drop formation conditions or by post-processing the particles, e.g. by cutting or dicing into other shapes. Particles can also be shaped by physical deformation followed by crosslinking. Particle shaping is described in U.S. Ser. No. 10/116,330 filed Apr. 4, 2002, the entire contents of which is hereby incorporated by reference.

Other embodiments are within the scope of the following claims.

What is claimed is:

1. An embolic composition, comprising:
substantially spherical embolic particles having a diameter of about 1500 micron or less, the particles comprising polyvinyl alcohol, and including a first region including pores having a first predominant pore size and a second region surrounding the first region and including pores having a second predominant pore size,
wherein the first predominant pore size is larger than the second predominant pore size.

2. The composition of claim 1 wherein the first predominant pore size is about 20 micron or more.

3. The composition of claim 1 wherein the first predominant pore size is about 30 micron or more.

4. The composition of claim 1 wherein the second region is about r to 0.8r, and r is a radius of the particles.

5. The composition of claim 1 wherein the second region is about r to 2r/3, and r is a radius of the particles.

6. The composition of claim 5 including a third region from about 2r/3 to r/3 and including pores having a third predominant pore size,
wherein the third predominant pore size is larger than the second predominant pore size and smaller than the first predominant pore size.

7. The composition of claim 6, wherein the first region is from about r/3 to C, and C is a center of the particles.

8. The composition of claim 7 wherein the first predominant pore size is about 20 micron or more.

9. The composition of claim 8 wherein the third predominant pore size is from about 2 to about 18 microns.

10. The composition of claim 1 wherein the second region is substantially free of pores greater than about 5 micron.

11. The composition of claim 1 wherein the predominant pore size generally, progressively increases from surface to the center of the particle.

12. The composition of claim 1 wherein the predominant pore size on the particle surface is about 1 micron or less.

13. The composition of claim 5, wherein the second predominant pore size is about 1 micron or less.

14. The composition of claim 13 wherein the second predominant pore size is about 0.1 micron or less.

15. The composition of claim 13 wherein the particles, interior of said second region, have a predominant pore size in the range of about 2 to 35 microns.

16. The composition of claim 14 wherein the first region is from about C to r/3 and the first predominant pore size is about 20 to 35 micron, and r is a radius of the particles.

17. The composition of claim 15 wherein the particles have a third region from r/3 to (2r)/3 and including pores having a third predominant pore size, in which the third predominant pore size is about 2 to 18 micron.

18. The composition of claim 1 wherein the second region is from about (2r)/3 to the surface and the second predominant pore size is about 10% or less than the first predominant pore size, and r is a radius of the particles.

19. The composition of claim 1 wherein the particles have a density of about 1.1 to about 1.4 g/cm$^3$.

20. The composition of claim 1 wherein the particles have a density of about 1.2 to 1.3 g/cm$^3$.

21. The composition of claim 1 wherein the embolic particles have a sphericity of about 90% or more.

22. The composition of claim 21 wherein the particles have an initial sphericity of about 97% or more.

23. The composition of claim 22 wherein the particles have a sphericity of about 0.90 after compression to about 50%.

24. The composition of claim 1 wherein the collection has a size uniformity of about ±15% or more.

25. The composition of claim 1 wherein the particles include about 1% or less polysaccharide.

26. The composition of claim 25 wherein the polysaccharide is alginate.

27. The composition of claim 26 wherein the alginate has a guluronic acid content of about 60% or greater.

28. The composition of claim 1 wherein the embolic particles are substantially insoluble in DMSO.

29. The composition of claim 1 wherein the embolic particles are substantially free of collagen.

30. The composition of claim 1 wherein the polyvinyl alcohol is composed of substantially unmodified polyvinyl alcohol prepolymer.

31. The composition of claim 1 wherein the polyvinyl alcohol is predominantly intrachain 1,3-diols acetalized.

32. The composition of claim 1 wherein the particles are suspended in a pharmaceutically acceptable medium.

33. The composition of claim 32 wherein the pharmaceutically acceptable medium comprises saline.

34. A method comprising administering to a patient in need of embolization a therapeutically effective amount of substantially spherical embolic polymer particles having a diameter of 1500 microns or less, the particles comprising polyvinyl alcohol, and including a first region including pores having a first predominant pore size and a second region surrounding the first region and including pores having a second predominant pore size,
wherein the first predominant pore size is larger than the second predominant pore size.

35. The method of claim 34 wherein the method of administration is by percutaneous injection.

36. The method of claim 34 wherein the method of administration is by a catheter.

37. The method of claim 34 wherein the particles are compressible, and are introduced to the body through a lumen, of a medical device, the lumen having a smaller diameter than the diameter of the uncompressed particles.

38. The method of claim 34 for treatment of uterine fibroids.

39. The method of claim 34 for treatment of a tumor.

40. The method of claim 34 for treatment of arteriovenous tumors.

41. An embolic composition, comprising:
embolic polymer particles having a diameter of about 1500 micron or less, and including a surface including pores with a predominant pore size of about 2 micron or less and pores interior to said surface with a predominant pore size of about 10 micron or more.

42. The composition of claim 41 wherein the particles include a surface region from about 0.8r to r wherein the predominate pore size is about 1 micron or less, and r is a radius of the particles.

43. The composition of claim 42 wherein particles include a region from about C to 0.8r which includes pores having a diameter of 10 microns or more.

44. The composition of claim 42 wherein the region C to 0.8r has a predominant pore size of about 3.5 to 2 micron.

45. An embolic composition comprising:

embolic polymer particles having a diameter of about 1500 microns or less, and including a surface region from about 0.8r to r, the predominant pore size in the surface region being smaller than the predominant pore size in a region C to 0.3r, and r is a radius of the particles.

46. An embolic composition, comprising:

embolic particles having a diameter of about 1500 microns or less, and including a surface region defined primarily by surface region pores and an interior region defined primarily by interior region pores, wherein the surface region pores are smaller than the interior region pores.

47. The composition of claim 45 or 46 wherein the embolic particles are substantially spherical.

48. The composition of claim 6, wherein the third predominant pore size is between 50% and 70% of the first predominant pore size.

* * * * *

UNITED STATES PATENT AND TRADEMARK OFFICE
CERTIFICATE OF CORRECTION

PATENT NO. : 7,588,780 B2 Page 1 of 1
APPLICATION NO. : 10/215594
DATED : September 15, 2009
INVENTOR(S) : Marcia S. Buiser et al.

It is certified that error appears in the above-identified patent and that said Letters Patent is hereby corrected as shown below:

On the Title Page, Item (56), Other Publications, Entry 1, Line 2: Delete "Processfor" and insert --Process for--.

On the Title Page, Item (57), Abstract, Line 4: After "particle" insert --.--.

Column 14, Claim 37, Line 53: Delete "lumen," and insert --lumen--.

Signed and Sealed this

Seventeenth Day of November, 2009

David J. Kappos
*Director of the United States Patent and Trademark Office*